(12) United States Patent
Nakafuji et al.

(10) Patent No.: US 9,581,905 B2
(45) Date of Patent: Feb. 28, 2017

(54) COMPOSITION FOR FILM FORMATION, RESIST UNDERLAYER FILM AND FORMING METHOD THEREOF, PATTERN-FORMING METHOD AND COMPOUND

(71) Applicant: JSR CORPORATION, Tokyo (JP)

(72) Inventors: Shin-ya Nakafuji, Tokyo (JP); Fumihiro Toyokawa, Tokyo (JP); Goji Wakamatsu, Tokyo (JP); Shingo Takasugi, Tokyo (JP); Tooru Kimura, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/959,223

(22) Filed: Dec. 4, 2015

(65) Prior Publication Data

US 2016/0085152 A1    Mar. 24, 2016

Related U.S. Application Data

(63) Continuation of application No. PCT/JP2014/065265, filed on Jun. 9, 2014.

(30) Foreign Application Priority Data

Jun. 24, 2013   (JP) .................. 2013-132125

(51) Int. Cl.
| | | |
|---|---|---|
| *G03F 7/16* | (2006.01) | |
| *G03F 7/36* | (2006.01) | |
| *G03F 7/11* | (2006.01) | |
| *C07C 33/38* | (2006.01) | |
| *C07C 15/50* | (2006.01) | |
| *C08F 38/00* | (2006.01) | |
| *C07C 33/28* | (2006.01) | |
| *C07C 39/21* | (2006.01) | |
| *C07C 43/215* | (2006.01) | |
| *C07C 25/24* | (2006.01) | |
| *H01L 21/027* | (2006.01) | |
| *C07C 211/50* | (2006.01) | |
| *C07C 211/58* | (2006.01) | |
| *C07C 15/54* | (2006.01) | |
| *C07C 15/58* | (2006.01) | |

(Continued)

(52) U.S. Cl.
CPC ............ *G03F 7/11* (2013.01); *C07C 15/14* (2013.01); *C07C 15/18* (2013.01); *C07C 15/50* (2013.01); *C07C 15/54* (2013.01); *C07C 15/58* (2013.01); *C07C 25/24* (2013.01); *C07C 33/28* (2013.01); *C07C 33/38* (2013.01); *C07C 39/21* (2013.01); *C07C 43/215* (2013.01); *C07C 211/50* (2013.01); *C07C 211/58* (2013.01);

(Continued)

(58) Field of Classification Search
CPC ......... C07C 15/50; C07C 15/54; C07C 15/58; H05K 3/027; H05K 3/281; H05K 3/3452; G03F 7/40; G03F 7/327; G03F 7/16; G03F 7/038; G03F 7/20; G03F 7/26; G03F 7/11; H01L 21/4846; H01L 21/31124; H01L 21/31133; H01L 21/31138

See application file for complete search history.

(56) References Cited

U.S. PATENT DOCUMENTS 6,423,811 B1 * 7/2002 Lau ................. C08G 61/02
528/125
2004/0198850 A1  10/2004 Connor et al.

(Continued)

FOREIGN PATENT DOCUMENTS

| JP | 2002-296789 A | 10/2002 |
|---|---|---|
| JP | 2004-504424 A | 2/2004 |

(Continued)

OTHER PUBLICATIONS

Yang et al "Ethynyl Aromatic Silicon hybridized Resin: Synthesis, Characterizations, and Thermal Properties", Journal of Applied Polymer Science, vol. 117, 714-719, 2010 Wiley Periodicals, Inc. Published online Mar. 23, 2010 in Wiley InterScience (www.interscience.wiley.com).*

(Continued)

*Primary Examiner* — Cynthia Hamilton
(74) *Attorney, Agent, or Firm* — Oblon, McClelland, Maier & Neustadt, L.L.P.

(57) ABSTRACT

A composition for film formation includes a compound represented by formula (1) and a solvent. In the formula (1), $R^1$, $R^2$ and $R^3$ each independently represent a group represented by the formula (a). In the formula (a), $R^A$ represents a hydrogen atom, an aryl group, or an alkyl group unsubstituted or substituted with at least one of a hydroxy group and an aryl group. $R^B$ represents a single bond or an arylene group. A part or all of hydrogen atoms on an aromatic ring of the aryl group and the arylene group may be substituted with a halogen atom, a hydroxy group, an amino group, a sulfanyl group, or a monovalent organic group having 1 to 20 carbon atoms and not including an aromatic ring.

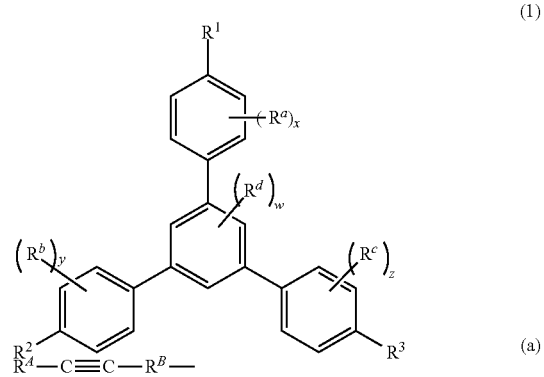

12 Claims, No Drawings

(51) Int. Cl.
    C07C 15/14    (2006.01)
    *C07C 15/18*    (2006.01)

(52) U.S. Cl.
    CPC .............. *C08F 38/00* (2013.01); *G03F 7/168* (2013.01); *G03F 7/36* (2013.01); *H01L 21/0271* (2013.01)

(56) References Cited

U.S. PATENT DOCUMENTS

2005/0074695 A1* 4/2005 Nakamura .............. G03F 7/091
                                                          430/271.1
2007/0195682 A1* 8/2007 Duerig ................. G11B 9/1454
                                                          369/126

FOREIGN PATENT DOCUMENTS

| JP | 2004-168748 A | 6/2004 |
| JP | 2004-177668 A | 6/2004 |
| JP | 2004-250585 A * | 9/2004 |
| JP | 2010-043176 A | 2/2010 |
| WO | WO 02/06366 A1 | 1/2002 |
| WO | WO 2012/103309 A2 | 8/2012 |

OTHER PUBLICATIONS

English translation of JP 2010-43176 A (2010) from machine translation from AIPN Japan Patent Office National Center for Industrial Property Information and Training, generated Mar. 18, 2016, 49 pages and 12 pages.*

English translation of JP 2004-250585 A (2004) from machine translation from AIPN Japan Patent Office National Center for Industrial Property Information and Training, generated Mar. 18, 2016, 25 pages and 2 pages.*

Shi et al, Polymers & polymer Composites, vol. 19, Nos. 2 & 3, 2011,, pp. 141-147.*

International Search Report issued Aug. 19, 2014, in PCT/JP2014/065265 filed Jun. 9, 2014 (w/ English translation).

* cited by examiner

COMPOSITION FOR FILM FORMATION, RESIST UNDERLAYER FILM AND FORMING METHOD THEREOF, PATTERN-FORMING METHOD AND COMPOUND

CROSS-REFERENCE TO RELATED APPLICATIONS

The present application is a continuation application of International Application No. PCT/JP2014/065265, filed Jun. 9, 2014, which claims priority to Japanese Patent Application No. 2013-132125, filed Jun. 24, 2013. The contents of these applications are incorporated herein by reference in their entirety.

BACKGROUND OF THE INVENTION

Field of the Invention

The present invention relates to a composition for film formation, a resist underlayer film and a forming method thereof, a pattern-forming method, and a compound.

Discussion of the Background

In producing semiconductor devices and the like, a multilayer resist process has been utilized to increase the degree of integration of the semiconductor devices. In this process, in general, a composition for resist underlayer film formation is applied first on the upper face side of a substrate to provide a resist underlayer film. Next, a resist pattern is formed on the upper face side of this resist underlayer film. Subsequently, the resist pattern is transferred to the resist underlayer film through etching, and further, the resist underlayer film pattern is transferred to the substrate, whereby a desired pattern can be obtained. The resist underlayer film for use in such a multilayer resist process is required to have general characteristics such as optical characteristics, e.g. an appropriate refractive index and an appropriate extinction coefficient, and favorable etching resistance.

In recent years, in order to further increase the degree of integration, further microfabrication of a pattern has been in progress. In order to address this microfabrication, various investigations have been made on the structure of a compound contained in the composition for resist underlayer film formation, etc., and a functional group and the like which may be included in the compound, etc. (see Japanese Unexamined Patent Application, Publication No. 2004-177668).

Recently, in the multilayer resist process described above, a method involving forming a hard mask on the resist underlayer film by way of a CVD technique has been investigated. Specifically, in this process, an inorganic hard mask as an intermediate layer is made on the resist underlayer film by way of a CVD technique. In such a case where the inorganic hard mask is made by way of the CVD technique, in particular, when a nitride-based film is to be made, the substrate needs to be heated to a temperature of at least 300° C., and typically 400° C.

Moreover, recently, a pattern has been more frequently formed on/in a substrate having a plurality of kinds of trenches, in particular, trenches differing from one another in terms of an aspect ratio. Even in the case of such a substrate, the resist underlayer film is required to be formed such that these trenches are sufficiently filled with the resist underlayer film and the resist underlayer film exhibits superior flatness.

SUMMARY OF THE INVENTION

According to one aspect of the present invention, a composition for film formation includes a compound represented by formula (1); and a solvent.

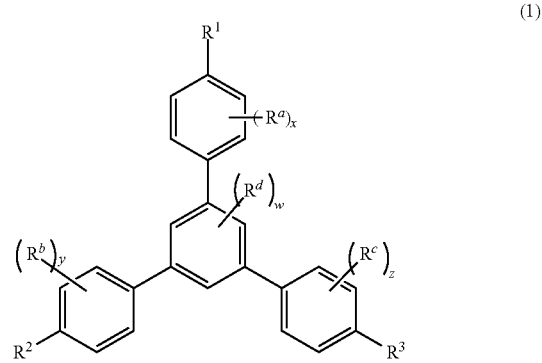

In the formula (1), $R^1$, $R^2$ and $R^3$ each independently represent a group represented by formula (a), wherein $R^1$, $R^2$ and $R^3$ are identical or different; $R^a$, $R^b$, $R^c$ and $R^d$ each independently represent a halogen atom, a hydroxy group, an amino group, a sulfanyl group, or a monovalent organic group having 1 to 20 carbon atoms and not including an aromatic ring; x, y and z are each independently an integer of 0 to 4; and w is an integer of 0 to 3. In a case where $R^a$ to $R^d$ are each present in a plurality of number, a plurality of $R^a$s are identical or different, a plurality of $R^b$s are identical or different, a plurality of $R^c$s are identical or different, and a plurality of $R^d$s are identical or different.

$$R^A\text{—}C\!\!\equiv\!\!C\text{—}R^B\text{—} \qquad (a)$$

In the formula (a), $R^A$ represents a hydrogen atom, an aryl group, or an alkyl group unsubstituted or substituted with at least one of a hydroxy group and an aryl group; and $R^B$ represents a single bond or an arylene group. A part or all of hydrogen atoms on an aromatic ring of the aryl group and the arylene group are unsubstituted or substituted with a halogen atom, a hydroxy group, an amino group, a sulfanyl group, or a monovalent organic group having 1 to 20 carbon atoms and not including an aromatic ring.

According to another aspect of the present invention, a resist underlayer film is formed from the composition.

According to further aspect of the present invention, a resist underlayer film-forming method includes applying the composition on an upper face side of a substrate to provide a coating film; and baking the coating film.

According to further aspect of the present invention, a pattern-forming method includes forming a resist pattern on an upper face side of a resist underlayer film which is formed by the resist underlayer film-forming method; and sequentially etching the resist underlayer film and a substrate using the resist pattern as a mask.

According to further aspect of the present invention, a compound is represented by formula (1').

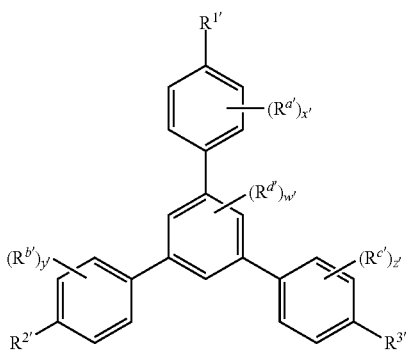

(1')

In the formula (1'), $R^1$, $R^2$ and $R^3$ each independently represent a group represented by formula (a'), wherein $R^1$, $R^2$ and $R^3$ are identical or different; $R^{a'}$, $R^{b'}$, $R^{c'}$ and $R^{d'}$ each independently represent a halogen atom, a hydroxy group, an amino group, a sulfanyl group, or a monovalent organic group having 1 to 20 carbon atoms and not including an aromatic ring; x', y' and z' are each independently an integer of 0 to 4; and w' is an integer of 0 to 3. In a case where $R^{a'}$ to $R^{d'}$ are each present in a plurality of number, a plurality of $R^{a'}$s are identical or different, a plurality of $R^{b'}$s are identical or different, a plurality of $R^{c'}$s are identical or different, and a plurality of $R^{d'}$s are identical or different.

(a')

In the formula (a'), $R^{A'}$ represents a hydrogen atom, an aryl group, or an alkyl group unsubstituted or substituted with at least one of a hydroxy group and an aryl group; and $R^{B'}$ represents a single bond or an arylene group. A part or all of hydrogen atoms on an aromatic ring of the aryl group and the arylene group are unsubstituted or substituted with a halogen atom, a hydroxy group, an amino group, a sulfanyl group, or a monovalent organic group having 1 to 20 carbon atoms and not including an aromatic ring, and at least one of three $R^{A'}$s in the compound represents a hydrogen atom.

DESCRIPTION OF THE EMBODIMENTS

According to an embodiment of the invention made for solving the aforementioned problems, a composition for film formation contains: a compound represented by the following formula (1) (hereinafter, may be also referred to as "(A) compound" or "compound (A)"); and a solvent (hereinafter, may be also referred to as "(B) solvent" or "solvent (B)"),

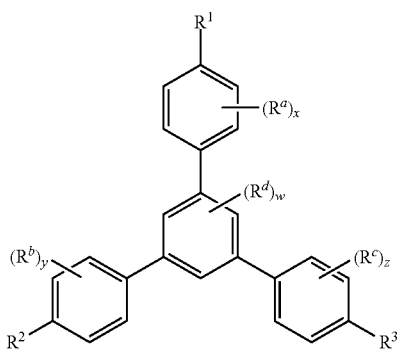

(1)

wherein in the formula (1), $R^1$, $R^2$ and $R^3$ each independently represent a group represented by the following formula (a), wherein $R^1$, $R^2$ and $R^3$ may be identical or different; $R^a$, $R^b$, $R^c$ and $R^d$ each independently represent a halogen atom, a hydroxy group, an amino group, a sulfanyl group, or a monovalent organic group having 1 to 20 carbon atoms and not including an aromatic ring; x, y and z are each independently an integer of 0 to 4; w is an integer of 0 to 3, wherein in a case where $R^a$ to $R^d$ are each present in a plurality of number, a plurality of $R^a$s may be identical or different, a plurality of $R^b$s may be identical or different, a plurality of $R^c$s may be identical or different, and a plurality of $R^d$s may be identical or different,

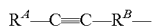

(a)

wherein in the formula (a), $R^A$ represents a hydrogen atom, an aryl group, or an alkyl group unsubstituted or substituted with at least one of a hydroxy group and an aryl group; and $R^B$ represents a single bond or an arylene group, wherein a part or all of hydrogen atoms on an aromatic ring of the aryl group and the arylene group may be substituted with a halogen atom, a hydroxy group, an amino group, a sulfanyl group, or a monovalent organic group having 1 to 20 carbon atoms and not including an aromatic ring.

According to another embodiment of the invention made for solving the aforementioned problems, a resist underlayer film is formed from the composition for film formation according to the embodiment of the invention.

According to still another embodiment of the invention made for solving the aforementioned problems, a resist underlayer film-forming method includes to the steps of: providing a coating film on the upper face side of a substrate; and baking the coating film, wherein the coating film is provided by using the film-forming composition according to the embodiment of the invention.

According to yet still another embodiment of the invention made for solving the aforementioned problems, a pattern-forming method includes the steps of: forming a resist pattern on the upper face side of a resist underlayer film; and sequentially etching the resist underlayer film and the substrate using the resist pattern as a mask, wherein the resist underlayer film is formed by the resist underlayer film-forming method according to the still another embodiment of the invention.

According to even yet still another embodiment of the invention made for solving the aforementioned problems, a compound is represented by the following formula (1').

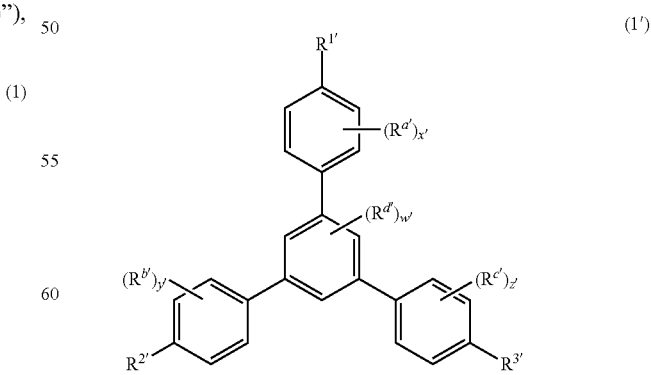

(1')

In the formula (1'), $R^1$, $R^2$ and $R^3$ each independently represent a group represented by the following formula (a'), wherein $R^1$, $R^2$ and $R^3$ may be identical or different; $R^{a'}$, $R^{b'}$, $R^{c'}$ and $R^{d'}$ each independently represent a halogen atom, a hydroxy group, an amino group, a sulfanyl group, or a monovalent organic group having 1 to 20 carbon atoms and not including an aromatic ring; x', y' and z' are each independently an integer of 0 to 4; and w' is an integer of 0 to 3, wherein in a case where $R^{a'}$ to $R^{d'}$ are each present in a plurality of number, a plurality of $R^a$'s may be identical or different, a plurality of $R^b$'s may be identical or different, a plurality of $R^c$'s may be identical or different, and a plurality of $R^d$'s may be identical or different.

$$R^{A'}—C≡C—R^{B'}— \quad (a')$$

In the formula (a'), $R^{A'}$ represents a hydrogen atom, an aryl group, or an alkyl group unsubstituted or substituted with at least one of a hydroxy group and an aryl group; and $R^{B'}$ represents a single bond or an arylene group, wherein a part or all of hydrogen atoms on an aromatic ring of the aryl group and the arylene group may be substituted with a halogen atom, a hydroxy group, an amino group, a sulfanyl group, or a monovalent organic group having 1 to 20 carbon atoms and not including an aromatic ring, and wherein at least one of three $R^{A'}$'s in the compound represents a hydrogen atom.

The composition for film formation and the resist underlayer film-forming method according to the embodiments of the present invention enable the formation of a resist underlayer film that exhibits superior heat resistance and superior flatness while satisfying the requirements for the general characteristics such as the optical characteristics and the etching resistance. The resist underlayer film according to the another embodiment of the present invention exhibits superior heat resistance and superior flatness while satisfying the requirements for the general characteristics such as the optical characteristics and the etching resistance. Therefore, a disadvantage such that a component of the resist underlayer film may be sublimated by the heating in the formation of the resist underlayer film and the sublimated component may adhere to the substrate again, resulting in the deterioration of the production yield of semiconductor devices, can be prevented. According to the pattern-forming method of the yet still another embodiment of the present invention, since the resist underlayer film exhibiting superior heat resistance and superior flatness is used, a favorable pattern can be formed. The compound according to the even yet still another embodiment of the present invention can be particularly suitably used as a component of the composition for film formation according to the embodiment of the present invention. Therefore, these can be suitably used in pattern formation that employs a multilayer resist process in the production of semiconductor devices in which microfabrication of patterns has been further in progress. Moreover, the composition for film formation according to the embodiment of the present invention can be suitably used in the aerospace industry in which superior heat resistance is required. Hereinafter, embodiments of the present invention will be described in detail.

Composition for Film Formation

The composition for film formation according to an embodiment of the present invention contains the compound (A) and the solvent (B). The composition for film formation may contain an acid generating agent (hereinafter, may be also referred to as "(C) acid generating agent" or "acid generating agent (C)"), a crosslinking agent (hereinafter, may be also referred to as "(D) crosslinking agent" or "crosslinking agent (D)") as a favorable component, and may contain other optional component within a range not leading to impairment of the effects of the present invention.

Due to containing the compound (A) and the solvent (B), the composition for film formation enables the formation of a resist underlayer film that exhibits superior heat resistance and superior flatness while satisfying the requirements for the general characteristics such as the optical characteristics and the etching resistance.

Although not necessarily clarified, the reason for achieving the above-described effects due to the composition for film formation having the constitution described above can be presumed as in the following, for example. Specifically, the compound (A) contained in the composition for film formation has a skeleton in which three benzene rings bond to the central benzene ring at 1, 3, and 5-positions of the central benzene ring, as represented by the above formula (1), and includes a group represented by the above formula (a) (hereinafter, may be also referred to as "group (a)") having a carbon-carbon triple bond, and the group (a) bonds to each of the three peripheral benzene rings at the para position with respect to the central benzene ring. Since the compound (A) has such a structure, the resulting resist underlayer film can satisfy the requirements for the general characteristics such as the optical characteristics and the etching resistance. In addition, the compound (A) can enhance the stability of the resist underlayer film, and as a result, the resist underlayer film can exhibit superior heat resistance. Furthermore, the compound (A) can have a molecule size which is appropriate, and uniform or extremely narrowly distributed. As a result, the resist underlayer film can exhibit superior flatness.

Hereinafter, each component will be explained.

(A) Compound

The compound (A) is represented by the following formula (1).

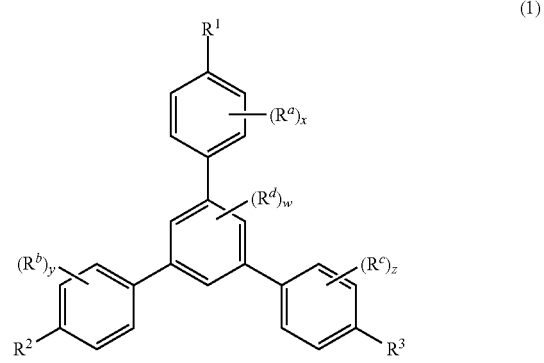

(1)

In the above formula (1), $R^1$, $R^2$ and $R^3$ each independently represent a group represented by the following formula (a), wherein $R^1$, $R^2$ and $R^3$ may be identical or different; $R^a$, $R^b$, $R^c$ and $R^d$ each independently represent a halogen atom, a hydroxy group, an amino group, a sulfanyl group, or a monovalent organic group having 1 to 20 carbon atoms and not including an aromatic ring; x, y and z are each independently an integer of 0 to 4; and w is an integer of 0 to 3, wherein in a case where $R^a$ to $R^d$ are each present in a plurality of number, a plurality of $R^a$'s may be identical or different, a plurality of $R^b$'s may be identical or different, a plurality of $R^c$'s may be identical or different, and a plurality of $R^d$'s may be identical or different.

$$R^A—C≡C—R^B— \quad (a)$$

In the above formula (a), $R^A$ represents a hydrogen atom, an aryl group, or an alkyl group unsubstituted or substituted with at least one of a hydroxy group and an aryl group; and $R^B$ represents a single bond or an arylene group, wherein a part or all of hydrogen atoms on an aromatic ring of the aryl group and the arylene group may be substituted with a halogen atom, a hydroxy group, an amino group, a sulfanyl group, or a monovalent organic group having 1 to 20 carbon atoms and not including an aromatic ring.

Examples of the aryl group which may be represented by $R^A$ include a phenyl group, a tolyl group, a xylyl group, a naphthyl group, an anthryl group, and the like. The aryl group has preferably 6 to 20 carbon atoms, and more preferably 6 to 10 carbon atoms. The aryl group is preferably a phenyl group or a naphthyl group, and more preferably a phenyl group.

Examples of the alkyl group which may be represented by $R^A$ include a methyl group, an ethyl group, a n-propyl group, an i-propyl group, a n-butyl group, an i-butyl group, a sec-butyl group, a t-butyl group, a n-pentyl group, a n-hexyl group, and the like. The alkyl group has preferably 1 to 10 carbon atoms, and more preferably 1 to 6 carbon atoms. In light of an improvement of the heat resistance of the resist underlayer film formed, the alkyl group is preferably a n-alkyl group, and more preferably a methyl group, an ethyl group, a n-propyl group or a n-butyl group.

Examples of the aryl group which may be present on the alkyl group as a substituent include groups similar to those exemplified in connection with the aryl group which may be represented by $R^A$, and the like.

Examples of the alkyl group substituted with the aryl group, which may be represented by $R^A$, include a benzyl group, a phenethyl group, a diphenylmethyl group, a diphenylethyl group, a dinaphthylmethyl group, and the like.

Examples of the alkyl group substituted with the hydroxy group, which may be represented by $R^A$, include a hydroxymethyl group, a hydroxyethyl group, a 2-hydroxy-2-propyl group, a dihydroxyethyl group, a 1,3-dihydroxy-2-propyl group, and the like.

Examples of the alkyl group substituted with the hydroxy group and the aryl group, which may be represented by $R^A$, include a hydroxyphenylmethyl group, a hydroxydiphenylmethyl group, a hydroxydiphenylethyl group, a dihydroxydiphenylethyl group, and the like.

Examples of the halogen atom which may substitute for a hydrogen atom on the aromatic ring of the aryl group include a fluorine atom, a chlorine atom, a bromine atom, an iodine atom, and the like. Of these, a fluorine atom and a chlorine atom are preferred, and a fluorine atom is more preferred.

The monovalent organic group having 1 to 20 carbon atoms and not including an aromatic ring, which may substitute for a hydrogen atom on the aromatic ring of the aryl group, is exemplified by: a monovalent chain hydrocarbon group having 1 to 20 carbon atoms; a monovalent alicyclic hydrocarbon group having 3 to 20 carbon atoms; a group (α) obtained from the chain hydrocarbon group or the alicyclic hydrocarbon group by incorporating a divalent hetero atom-containing group between adjacent two carbon atoms thereof; a group obtained from the chain hydrocarbon group, the alicyclic hydrocarbon group or the group (α) by substituting a part or all of hydrogen atoms included therein with a hetero atom-containing monovalent group not including an aromatic ring; and the like.

Examples of the chain hydrocarbon group include:

alkyl groups such as a methyl group, an ethyl group, a propyl group and a butyl group;

alkenyl groups such as an ethenyl group, a propenyl group and a butenyl group;

alkynyl groups such as an ethynyl group, a propynyl group and a butynyl group; and the like.

Examples of the alicyclic hydrocarbon group include:

cycloalkyl groups such as a cyclopropyl group, a cyclobutyl group, a cyclopentyl group, a cyclohexyl group, a cyclooctyl group, a norbornyl group and an adamantyl group;

cycloalkenyl groups such as a cyclopropenyl group, a cyclobutenyl group, a cyclopentenyl group, a cyclohexenyl group, a cyclooctenyl group and a norbornenyl group; and the like.

Examples of the divalent hetero atom-containing group include —O—, —NR"—, wherein R" represents a chain hydrocarbon group having 1 to 10 carbon atoms or an alicyclic hydrocarbon group having 3 to 10 carbon atoms, —S—, a carbonyl group, a carbonyloxy group, a carbonylamino group, a sulfonamide group, and the like.

Examples of the hetero atom-containing monovalent group include a halogen atom, a hydroxy group, an amino group, a sulfanyl group, a cyano group, a nitro group, an aminosulfonyl group, and the like.

The group which may substitute for a hydrogen atom on the aromatic ring of the aryl group is preferably a hydroxy group, an amino group, or a monovalent organic group having 1 to 20 carbon atoms and not including an aromatic ring, more preferably a hydroxy group, an amino group, a hydroxyalkyl group, an alkoxy group, or a cycloalkyloxy group, and still more preferably a hydroxy group, an amino group, a hydroxymethyl group, a methoxy group or an ethoxy group.

In light of the improvement of the heat resistance of the resist underlayer film formed, $R^A$ represents preferably a hydrogen atom, an unsubstituted aryl group having 6 to 20 carbon atoms, an aryl group having 6 to 20 carbon atoms and being substituted with a hydroxy group or an amino group, an unsubstituted alkyl group having 1 to 10 carbon atoms, an alkyl group having 1 to 10 carbon atoms and being substituted with a hydroxy group, or an alkyl group having 1 to 10 carbon atoms and being substituted with a hydroxy group and an aryl group, and more preferably a phenyl group, a hydroxymethyl group, a 2-hydroxy-2-propyl group, a hydroxydiphenylmethyl group, or a phenyl group substituted with an amino group.

Examples of the arylene group which may be represented by $R^B$ include a phenylene group, a tolylene group, a xylylene group, a naphthylene group, an anthrylene group, and the like. The arylene group has preferably 6 to 20 carbon atoms, and more preferably 6 to 10 carbon atoms. The arylene group is preferably a phenylene group or a naphthylene group, and more preferably a phenylene group.

Examples of the halogen atom and the monovalent organic group having 1 to 20 carbon atoms and not including an aromatic ring, both of which may substitute for a hydrogen atom on the aromatic ring of the arylene group, include groups similar to those exemplified in connection with the halogen atom and the monovalent organic group both of which may substitute for a hydrogen atom on the aromatic ring of the aryl group which may be represented by $R^A$, and the like.

In light of the improvement of the heat resistance of the resist underlayer film formed, $R^B$ represents preferably a single bond, or an unsubstituted arylene group having 6 to 10 carbon atoms, and more preferably a single bond or a phenylene group.

Examples of the halogen atom and the monovalent organic group having 1 to 20 carbon atoms and not including an aromatic ring, which may be represented by $R^a$ to $R^d$ in the above formula (1), include groups similar to those exemplified in connection with the halogen atom and the monovalent organic group, which may be present as a substituent on the aryl group and the arylene group in the above formula (a), and the like.

$R^a$ to $R^d$ in the above formula (1) each independently represent preferably a halogen atom, or a monovalent organic group having 1 to 20 carbon atoms and not including an aromatic ring, more preferably a halogen atom, an alkyl group having 1 to 10 carbon atoms, or a hydroxyalkyl group having 1 to 10 carbon atoms, and still more preferably a fluorine atom, a methyl group, an ethyl group or a hydroxymethyl group.

In light of the improvement of the heat resistance of the resist underlayer film formed, x, y, z and w in the above formula (1) are an integer of preferably 0 to 2, more preferably 0 or 1, and still more preferably 0. In light of the improvement of the heat resistance of the resist underlayer film formed, it is preferred that the aromatic ring in the aryl group and the arylene group of the above formula (a) does not have the substituent described above.

Although $R^1$, $R^2$ and $R^3$ in the above formula (1) may be identical or different, $R^1$, $R^2$ and $R^3$ are preferably identical in light of an improvement of the flatness of the resist underlayer film formed, and/or in light of the ease in synthesis of the compound (A).

In a case where $R^B$ represents a single bond and $R^A$ does not represent a hydrogen atom, the compound (A) is exemplified by compounds represented by the following formulae (1-1-1) to (1-1-12) (hereinafter, may be also referred to as "compounds (I-1-1) to (I-1-12)"), and the like.

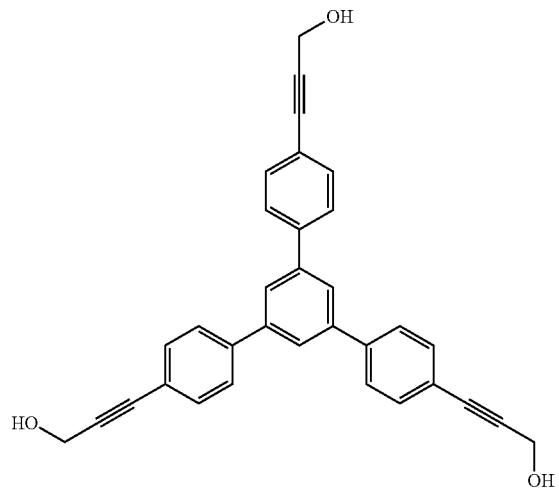

(1-1-2)

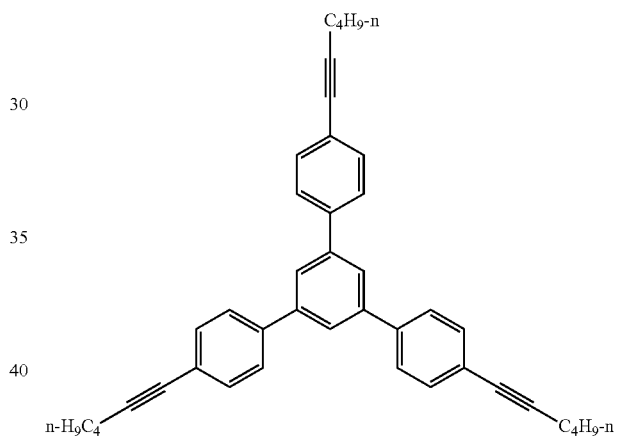

(1-1-3)

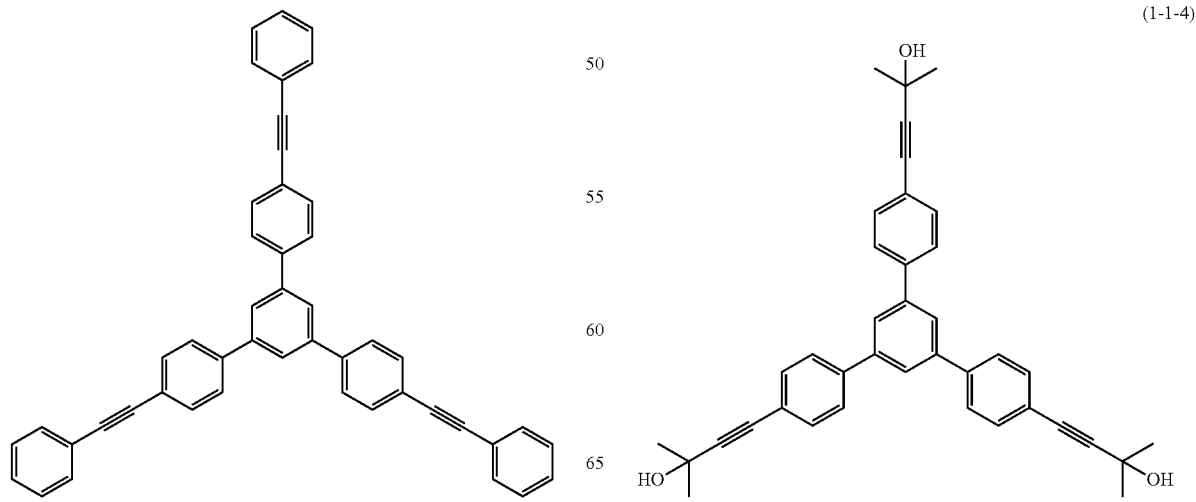

(1-1-1)

(1-1-4)

(1-1-5)
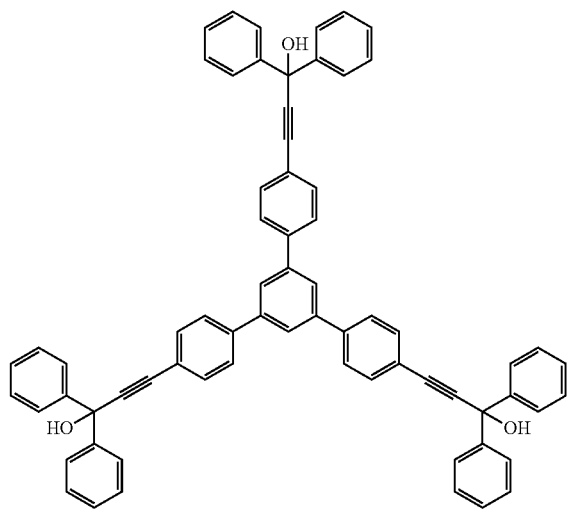
(1-1-6)
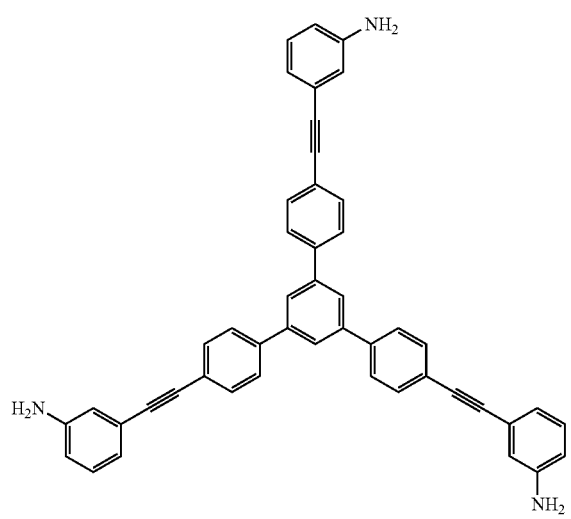
(1-1-7)
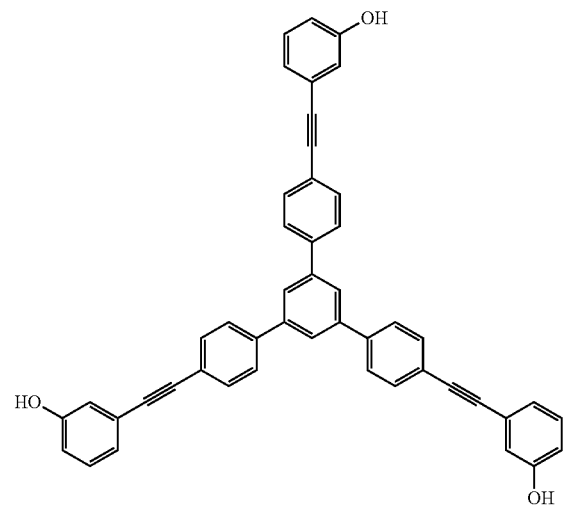
(1-1-8)
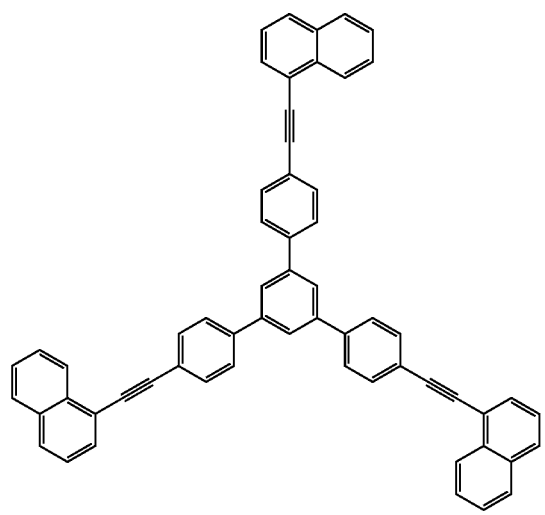
(1-1-9)
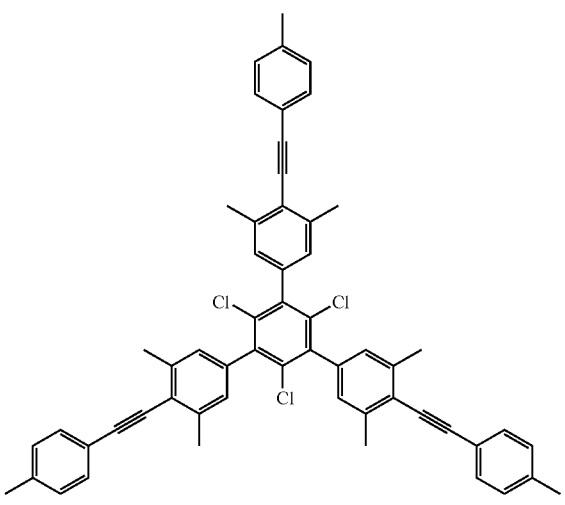
(1-1-10)

(1-1-11)
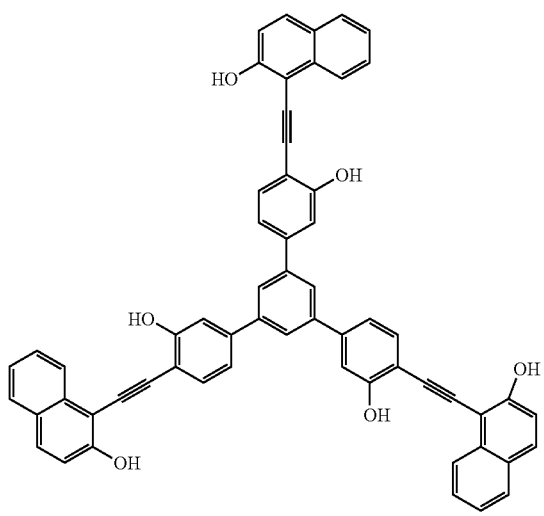
(1-1-12)
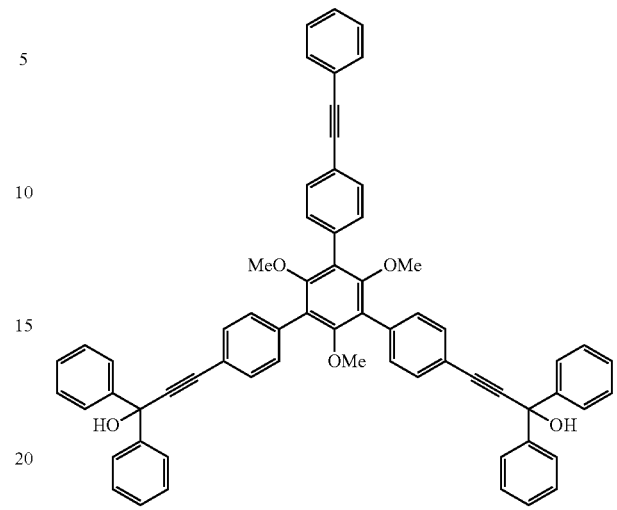
In a case where $R^B$ does not represent a single bond and $R^A$ does not represent a hydrogen atom, the compound (A) is exemplified by compounds represented by the following formulae (1-2-1) to (1-2-8) (hereinafter, may be also referred to as "compounds (I-2-1) to (I-2-8)"), and the like.
(1-2-1)
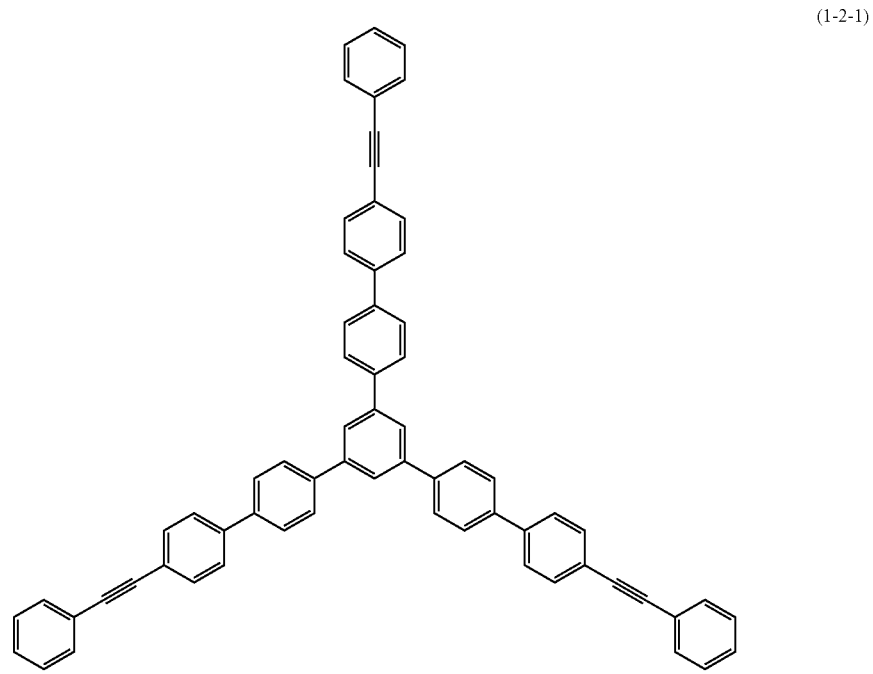

(1-2-2)
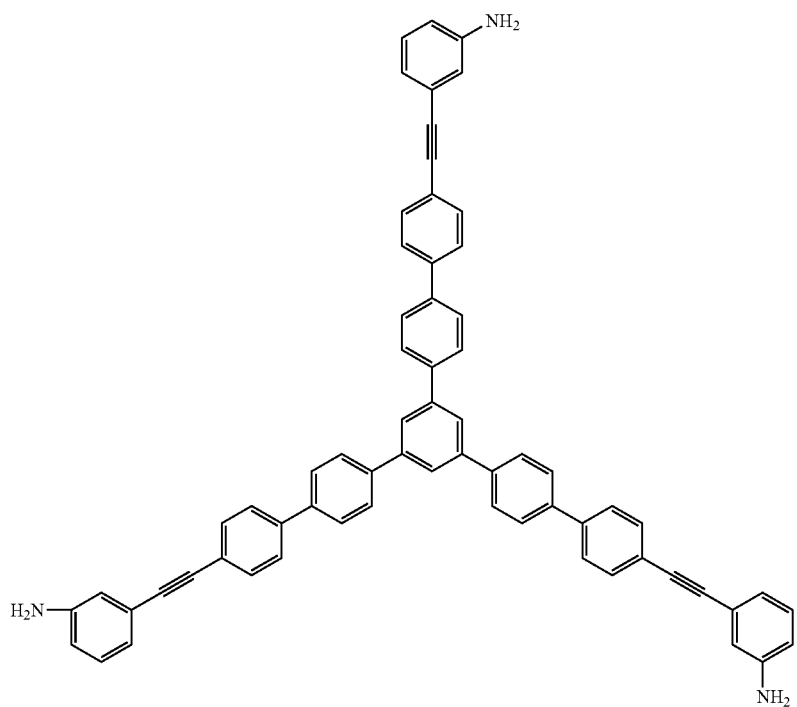
(1-2-3)
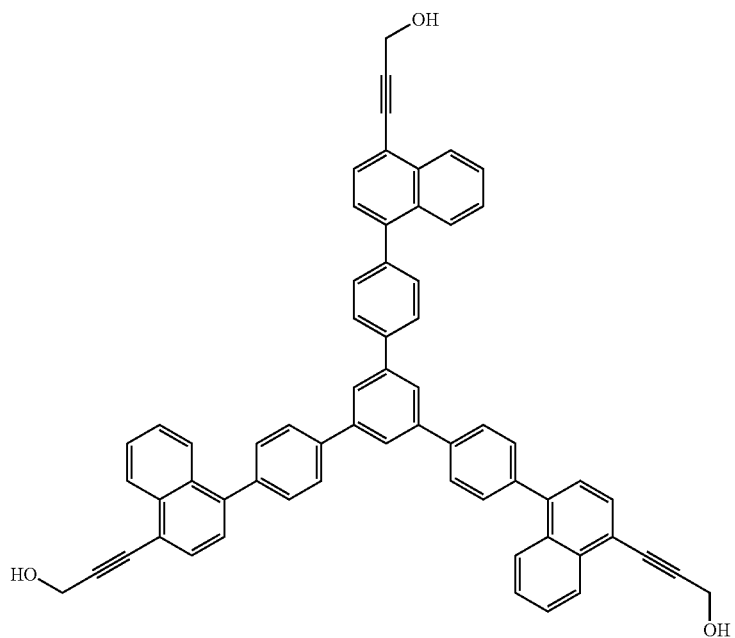

(1-2-4)
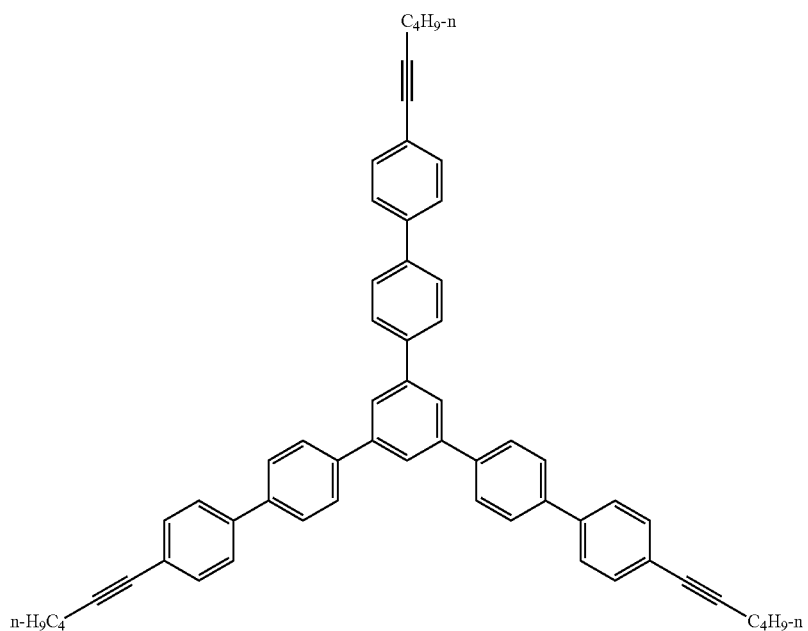
(1-2-5)
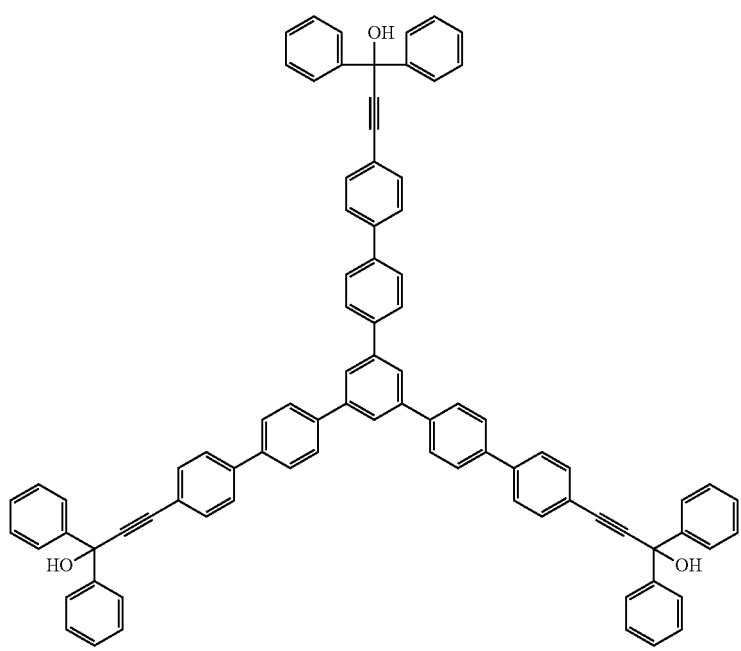

(1-2-6)
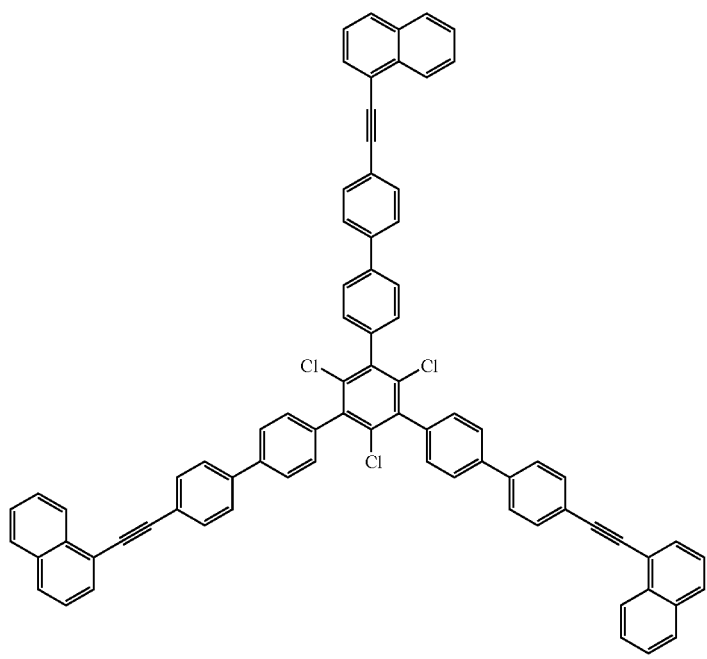
(1-2-7)
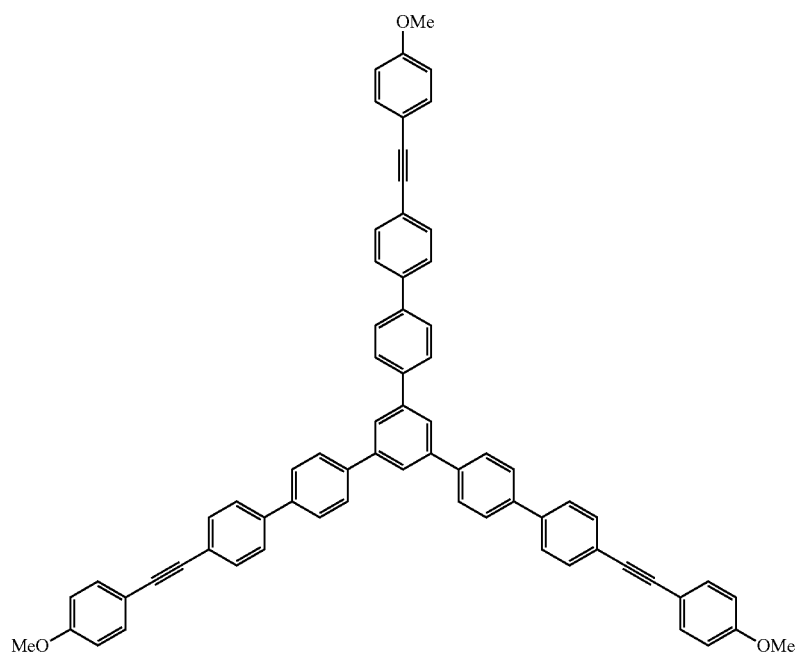

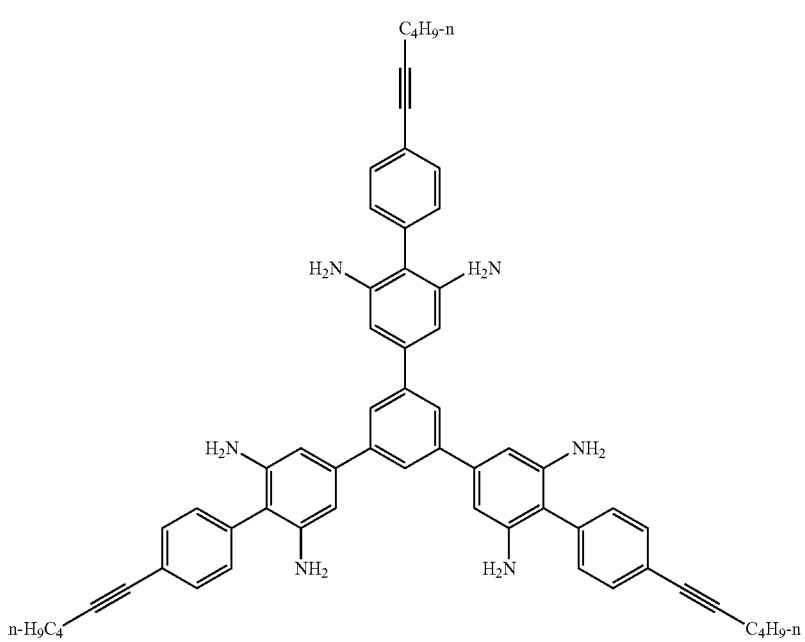

(1-2-8)

A more preferred embodiment of the compound (A) is exemplified by a compound represented by the following formula (1') (hereinafter, may be also referred to as "compound (I')"), i.e., the compound (A) in which at least one of $R^A$s represents a hydrogen atom. According to the compound (A) thus having a carbon-carbon triple bond on its terminus, curing properties through crosslinking can be further enhanced.

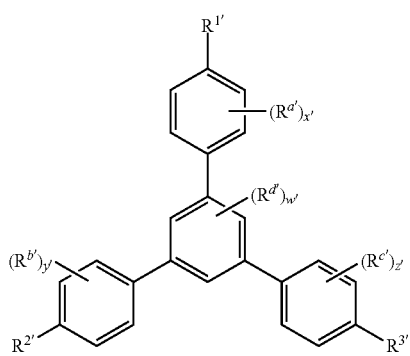

(1')

In the above formula (1'), $R^1$, $R^2$ and $R^3$ each independently represent a group represented by the following formula (a'), wherein $R^1$, $R^2$ and $R^3$ may be identical or different; $R^{a'}$, $R^{b'}$, $R^{c'}$ and $R^{d'}$ each independently represent a halogen atom, a hydroxy group, an amino group, a sulfanyl group, or a monovalent organic group having 1 to 20 carbon atoms and not including an aromatic ring; x', y' and z' are each independently an integer of 0 to 4; and w' is an integer of 0 to 3, wherein in a case where $R^{a'}$ to $R^{d'}$ are each present in a plurality of number, a plurality of $R^{a'}$s may be identical or different, a plurality of $R^{b'}$s may be identical or different, a plurality of $R^{c'}$s may be identical or different, and a plurality of $R^{d'}$s may be identical or different.

$$R^{A'}-C{\equiv}C-R^{B'}- \qquad (a')$$

In the above formula (a'), $R^{A'}$ represents a hydrogen atom, an aryl group, or an alkyl group unsubstituted or substituted with at least one of a hydroxy group and an aryl group; and $R^{B'}$ represents a single bond or an arylene group, wherein a part or all of hydrogen atoms on an aromatic ring of the aryl group and the arylene group may be substituted with a halogen atom, a hydroxy group, an amino group, a sulfanyl group, or a monovalent organic group having 1 to 20 carbon atoms and not including an aromatic ring, and wherein at least one of three $R^A$s in the compound represents a hydrogen atom.

$R^{a'}$ to $R^{d'}$ and x' to w' in the above formula (1') and $R^{A'}$ and $R^{B'}$ in the above formula (a') are exemplified by groups similar to those respectively exemplified in connection with $R^a$ to $R^d$ and x to w the above formula (1) and $R^A$ and $R^B$ in the above formula (a), and the like.

In regard to the three $R^A$s in the compound (I'), in light of further enhancement of the curing properties of the composition for film formation, preferably two or more of the three $R^A$s, and more preferably all the three $R^A$s represent a hydrogen atom.

Examples of the compound (I') include compounds represented by the following formulae (1-3-1) to (1-3-8) (hereinafter, may be also referred to as "compounds (I-3-1) to (I-3-8)"), and the like.

(1-3-1)
(1-3-2)
(1-3-3)
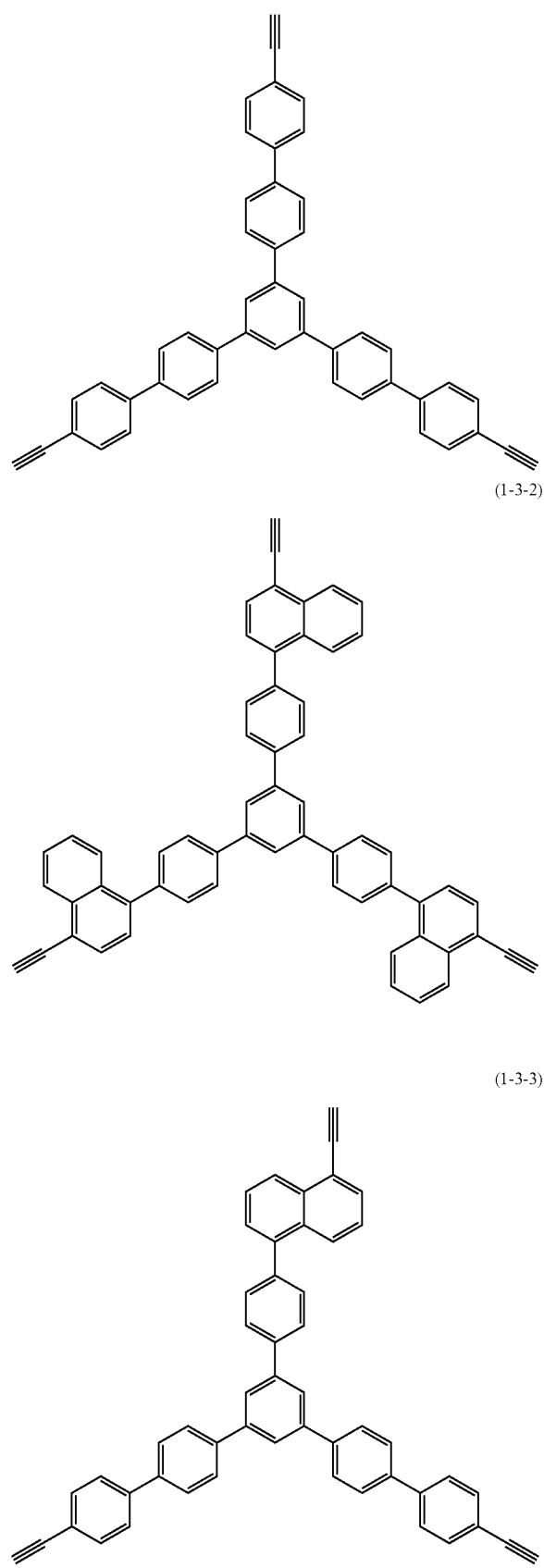
(1-3-4)
(1-3-5)
(1-3-6)
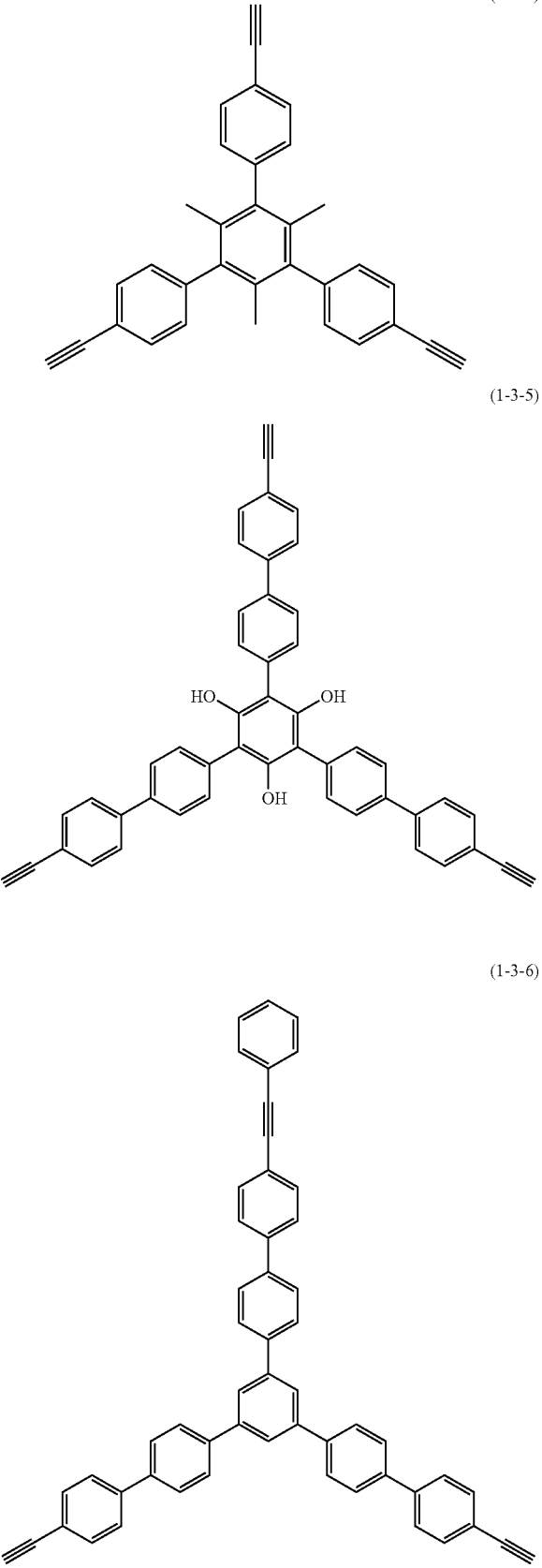

-continued (1-3-7)

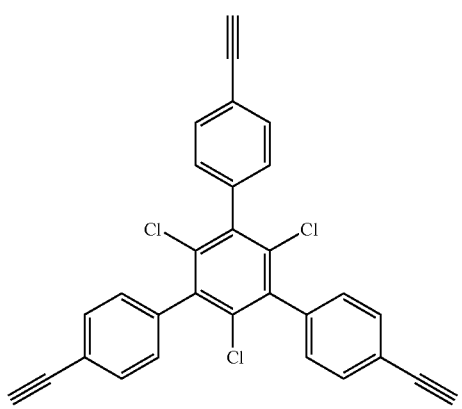

(1-3-8)

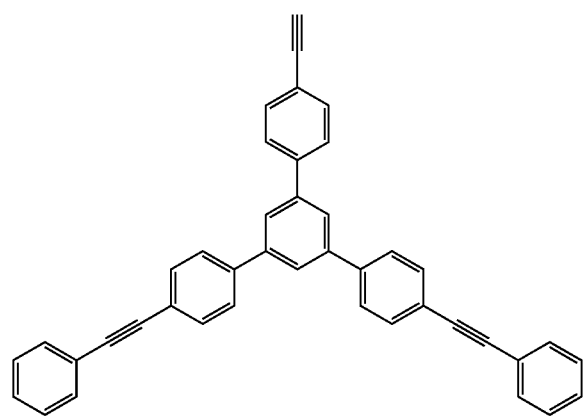

Of these, the compounds (I-1-1) to (I-1-6), and the compound (I-3-1) are preferred.

For example, in the case of the compound (A) in which $R^B$ in the group (a) represents a single bond and $R^A$ in the group (a) does not represent a hydrogen atom (a compound represented by the following formula (1-A)), the compound (A) can be synthesized according to the following reaction scheme.

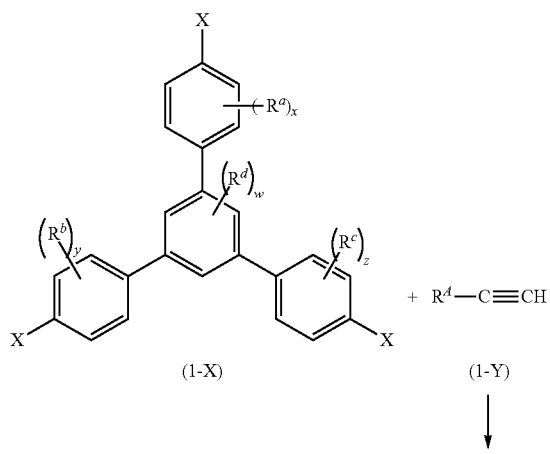

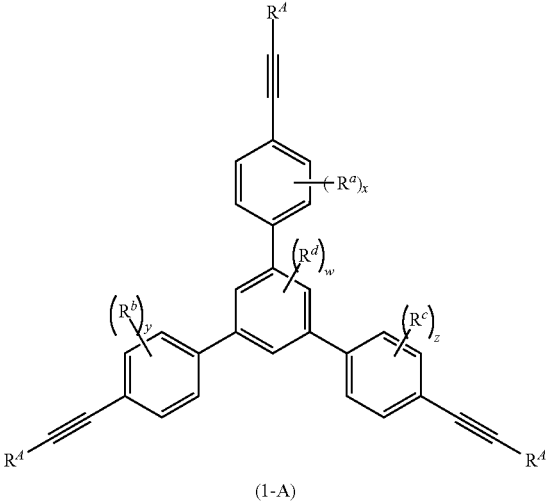

(1-A)

In the above scheme, X represents a halogen atom; $R^A$ represents an aryl group, or an alkyl group unsubstituted or substituted with at least one of a hydroxy group and an aryl group, wherein a plurality of Xs may be identical or different and a plurality of $R^A$s may be identical or different; $R^a$, $R^b$, $R^c$ and $R^d$ each independently represent a halogen atom, a hydroxy group, an amino group, a sulfanyl group, or a monovalent organic group having 1 to 20 carbon atoms and not including an aromatic ring; x, y and z are each independently an integer of 0 to 4; and w is an integer of 0 to 3, wherein in a case where $R^a$ to $R^d$ are each present in a plurality of number, a plurality of $R^a$s may be identical or different, a plurality of $R^b$s may be identical or different, a plurality of $R^c$s may be identical or different, and a plurality of $R^d$s may be identical or different, and wherein a part or all of hydrogen atoms on an aromatic ring of the aryl group may be substituted with a halogen atom, a hydroxy group, an amino group, a sulfanyl group, or a monovalent organic group having 1 to 20 carbon atoms and not including an aromatic ring.

The compound represented by the above formula (1-A) can be obtained by reacting the compound represented by the above formula (1-X) (1,3,5-tris(p-halophenyl)benzene) with an ethynyl compound represented by the above formula (1-Y) in the presence of a palladium catalyst such as dichlorobis(triphenylphosphine)palladium(II), a copper(I) catalyst such as copper(I) iodide, and a base such as triethylamine, in a solvent such as tetrahydrofuran. The resulting product may be purified through reprecipitation, recrystallization, washing, column chromatography, and/or the like.

In light of an improvement of a yield of the compound (A), X represents preferably a chlorine atom, a bromine atom, or an iodine atom, and more preferably a bromine atom.

The compound (A) in which $R^B$ in the group (a) represents an arylene group and $R^A$ in the group (a) does not represent a hydrogen atom can be synthesized by using, for example, 1,3,5-tris(4'-halobiphenyl-4-yl)benzene or the like in place of the compound (1-X).

The compound (A) in which $R^A$ in the group (a) represents a hydrogen atom can be synthesized by reacting a silylated acetylene compound such as trimethylsilylacetylene with the compound (1-X) or the like to give a reaction product, and thereafter subjecting this reaction product to desilylation in a solvent such as a mixture of tetrahydrofuran and methanol, in the presence of a base such as potassium carbonate.

The compound (A) other than those described above can also be synthesized according to a method similar to the methods described above.

In light of the improvement of the heat resistance of the resist underlayer film formed, the lower limit of the molecular weight of the compound (A) is preferably 400, more preferably 450, still more preferably 500, and particularly preferably 550. In light of the improvement of the flatness of the resist underlayer film formed, the upper limit of the molecular weight of the compound (A) is preferably 1,000, preferably 900, still more preferably 800, and particularly preferably 700.

The lower limit of the carbon percentage content of the compound (A) is preferably 50 atom %, more preferably 55 atom %, and still more preferably 60 atom %. In addition, the lower limit of the carbon percentage content of the compound (A) is preferably 80% by mass, more preferably 85% by mass, and still more preferably 90% by mass. A higher carbon percentage content is more preferred.

When the carbon percentage content of the compound (A) falls within the above range, the heat resistance of the resist underlayer film formed can be further improved.

The content of the compound (A) in the composition for film formation is preferably no less than 80% by mass, more preferably no less than 90% by mass, and still more preferably no less than 95% by mass with respect to the total solid content.

(B) Solvent

The solvent (B) is not particularly limited as long as the solvent (B) is capable of dissolving or dispersing the compound (A) and an optional component contained as desired.

The solvent (B) is exemplified by an alcohol solvent, an ether solvent, a ketone solvent, an amide solvent, an ester solvent, a hydrocarbon solvent, and the like.

Examples of the alcohol solvent include:
aliphatic monohydric alcohol solvents having 1 to 18 carbon atoms such as 4-methyl-2-pentanol and n-hexanol;
alicyclic monohydric alcohol solvents having 3 to 18 carbon atoms such as cyclohexanol;
polyhydric alcohol solvents having 2 to 18 carbon atoms such as 1,2-propylene glycol;
polyhydric alcohol partial ether solvents having 3 to 19 carbon atoms, such as propylene glycol monomethyl ether; and the like.

Examples of the ether solvent include:
dialkyl ether solvents such as diethyl ether, dipropyl ether and dibutyl ether;
cyclic ether solvents such as tetrahydrofuran and tetrahydropyran;
aromatic ring-containing ether solvents such as diphenyl ether and anisole; and the like.

Examples of the ketone solvent include:
chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone and trimethylnonanone;
cyclic ketone solvents such as cyclopentanone, cyclohexanone, cycloheptanone, cyclooctanone and methylcyclohexanone;
2,4-pentanedione, acetonylacetone, and acetophenone; and the like.

Examples of the amide solvent include:
cyclic amide solvents such as N,N'-dimethylimidazolidinone and N-methylpyrrolidone;
chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:
monocarboxylic acid ester solvents, e.g., acetic acid esters such as n-butyl acetate;
polyhydric alcohol carboxylate solvents such as propylene glycol acetate;
polyhydric alcohol partial ether carboxylate solvents, e.g., polyhydric alcohol partial alkyl ether acetates such as propylene glycol monomethyl ether acetate;
polyhydric carboxylic acid diester solvents such as diethyl oxalate;
lactone solvents such as γ-butyrolactone and δ-valerolactone;
carbonate solvents such as diethyl carbonate, ethylene carbonate and propylene carbonate; and the like.

Examples of the hydrocarbon solvent include: linear or branched chain hydrocarbons having 5 to 10 carbon atoms; alicyclic hydrocarbons having 5 to 12 carbon atoms; aromatic hydrocarbons having 6 to 18 carbon atoms, and the like. A part or all of hydrogen atoms on a ring of the alicyclic hydrocarbons and the aromatic hydrocarbons may be substituted with a linear or branched alkyl group having 1 to 5 carbon atoms.

Of these, a ketone solvent is preferred, a cyclic ketone solvent is more preferred, and cyclohexanone is still more preferred. The composition for film formation may contain one type, or two or more types of the solvent (B).

(C) Acid Generating Agent

The acid generating agent (C) is a component that generates an acid upon exposure or heating. When the composition for film formation contains the acid generating agent (C), a crosslinking reaction may be allowed to proceed between the molecules of the compound (A) at comparatively low temperatures including normal temperatures.

Examples of the acid generating agent that generates an acid upon an exposure (hereinafter, may be also referred to as "photoacid generating agent") include those described in paragraphs [0077] to [0081] of Japanese Unexamined Patent Application, Publication No. 2004-168748, and the like.

In addition, examples of the acid generating agent that generates an acid upon heating (hereinafter, may be also referred to as "thermal acid generating agent") include 2,4,4,6-tetrabromocyclohexadienone, benzoin tosylate, 2-nitrobenzyl tosylate, alkylsulfonates, and the like in addition to the onium salt-type acid generating agents exemplified as the photoacid generating agent described above.

Among these acid generating agents (C), thermal acid generating agents are preferred, onium salt-type acid generating agents are more preferred, iodonium salt-type acid generating agents are still more preferred, diphenyliodonium trifluoromethanesulfonate, diphenyliodonium nonafluoro-n-butanesulfonate, diphenyliodonium pyrenesulfonate, diphenyliodonium n-dodecylbenzenesulfonate, diphenyliodonium 10-camphorsulfonate, diphenyliodonium naphthalenesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium n-dodecylbenzenesulfonate, bis(4-t-butylphenyl)iodonium 10-camphorsulfonate and bis(4-t-butylphenyl)iodonium naphthalenesulfonate are particularly preferred, and bis(4-t-butylphenyl)iodonium nonafluoro-n-butanesulfonate is further particularly preferred.

The content of the acid generating agent (C) is preferably no greater than 5,000 parts by mass, more preferably 0.1 parts by mass to 500 parts by mass, still more preferably 0.5 parts by mass to 100 parts by mass, and particularly preferably 1 part by mass to 20 parts by mass with respect to 100 parts by mass of the compound (A). When the content of the acid generating agent (C) falls within the above range, the strength of the resist underlayer film formed from the composition for film formation can be more enhanced. One type, or two or more types of the acid generating agent (C) may be used. Moreover, the photoacid generating agent and the thermal acid generating agent may be used in combination as the acid generating agent (C).

(D) Crosslinking Agent

The crosslinking agent (D) is a compound that includes a crosslinkable group. When the composition for film formation contains the crosslinking agent (D), crosslinking between the molecules of the compound (A) can be 1 to achieved more effectively.

The crosslinking agent (D) preferably includes two or more crosslinkable groups.

The crosslinking agent (D) is exemplified by a polynuclear phenol, an alkoxymethylated melamine, an alkoxymethylated glycoluril, a diisocyanate, a compound represented by the following formula (d) (hereinafter, may be also referred to as "compound (d)"), and the like.

In the above formula (d), Ar represents an aromatic hydrocarbon group having a valency of n or a heteroaromatic group having a valency of n; Y represents a carbonyl group or a sulfonyl group; Q represents a monovalent heteroaromatic group or $-OR^4$, wherein $R^4$ represents a monovalent organic group having 1 to 30 carbon atoms; and n is an integer of 2 to 7, wherein a plurality of Ys may be identical or different, and a plurality of Qs may be identical or different.

It is presumed that when the compound (d) is used as the crosslinking agent (D), the crosslinking agent (D) would react with the compound (A), leading to the formation of a carbonyl group or a sulfonyl group situated between the aromatic rings, and consequently, the heat resistance of the resist underlayer film formed from the composition for film formation would be more improved. In addition, a more appropriate refractive index and a more appropriate extinction coefficient would be achieved.

Examples of the aromatic hydrocarbon group having a valency of n which may be represented by Ar include: groups obtained from an aromatic hydrocarbon such as benzene, toluene, xylene, naphthalene, anthracene, indene and fluorenylidenebiphenyl by eliminating therefrom n hydrogen atoms bound to the aromatic ring; and the like.

Examples of the heteroaromatic group having a valency of n which may be represented by Ar include groups obtained from a heteroaromatic compound such as furan, pyrrole, thiophene, phosphole, pyrazole, oxazole, isoxazole, thiazole, pyridine, pyrazine, pyrimidine, pyridazine or triazine by eliminating therefrom n hydrogen atoms bound to the heteroaromatic ring.

Preferably, Y represents a carbonyl group.

Examples of the monovalent heteroaromatic group which may be represented by Q include groups obtained by adding (n−1) hydrogen atoms to the groups exemplified in connection with the heteroaromatic group having a valency of n which may be represented by Ar, and the like.

Examples of the monovalent organic group having 1 to 30 carbon atoms represented by $R^4$ of $-OR^4$ in Q include groups represented by the following formulae (i) to (iii) (hereinafter, may be also referred to as "groups (i) to (iii)"), and the like.

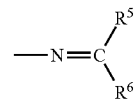

In the above formula (i), $R^5$ and $R^6$ each independently represent a monovalent organic group having 1 to 20 carbon atoms, or $R^5$ and $R^6$ taken together represent a ring structure having 3 to 20 ring atoms, together with the carbon atom to which $R^5$ and $R^6$ bond.

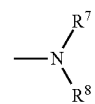

In the above formula (ii), $R^7$ and $R^8$ each independently represent a monovalent organic group having 1 to 20 carbon atoms, or $R^7$ and $R^8$ taken together represent a ring structure having 3 to 20 ring atoms, together with the nitrogen atom to which $R^7$ and $R^8$ bond.

In the above formula (iii), $R^9$ represents a monovalent organic group having 1 to 20 carbon atoms and including an electron-withdrawing group.

Examples of the monovalent organic group having 1 to 20 carbon atoms which may be represented by $R^5$ to $R^8$ include: monovalent hydrocarbon groups having 1 to 20 carbon atoms; hetero atom-containing groups obtained from the hydrocarbon groups by combining the hydrocarbon groups with at least one group selected from the set consisting of $-CO-$, $-COO-$, $-O-$, $-NR'-$, $-CS-$, $-S-$, $-SO-$ and $-SO_2-$; groups obtained from the hydrocarbon groups or the hetero atom-containing groups by substituting a part or all of hydrogen atoms included in the hydrocarbon groups or the hetero atom-containing groups with a fluorine atom, a hydroxy group, a carboxy group, a cyano group, etc.; and the like, wherein R' represents a hydrogen atom or a monovalent hydrocarbon group having 1 to 20 carbon atoms.

Examples of the monovalent hydrocarbon group having 1 to 20 carbon atoms include:

chain hydrocarbon groups having 1 to 20 carbon atoms, e.g. alkyl groups such as a methyl group, an ethyl group and a propyl group, alkenyl groups such as an ethenyl group and a propenyl group, and alkynyl groups such as an ethynyl group and a propynyl group;

alicyclic hydrocarbon group having 3 to 20 carbon atoms, e.g. cycloalkyl groups such as a cyclopropyl group, a cyclobutyl group, a cyclopentyl group and a norbornyl group; a cyclopropenyl group, a cyclobutenyl group, a cyclopentenyl group, and a norbornyl group;

aromatic hydrocarbon groups having 6 to 20 carbon atoms, e.g. aryl groups such as a phenyl group, a tolyl group, a xylyl group and a naphthyl group, aralkyl groups such as a benzyl group and a naphthylmethyl group; and the like.

Exampled of the ring structure having 3 to 20 ring atoms which may be taken together represented by $R^5$ and $R^6$, together with the carbon atom to which R⁵ and R⁶ bond include cyclopropane structures, cyclobutane structures, cyclopentane structures, cyclohexane structures, and the like.

Examples of the ring structure having 3 to 20 ring atoms which may be taken together represented by R⁷ and R⁸, together with the nitrogen atom to which R⁷ and R⁸ bond include azacyclopropane structures, azacyclobutane structures, azacyclopentane structures, azacyclohexane structures, and the like.

Examples of the monovalent organic group, which is represented by R⁹, having 1 to 20 carbon atoms and including an electron-withdrawing group include monovalent hydrocarbon groups having 1 to 20 carbon atoms in which a part or all of hydrogen atom thereof is substituted with an electron-withdrawing group, and the like. Examples of the electron-withdrawing group include halogen atoms such as a fluorine atom and a chlorine atom, a nitro group, a cyano group, and the like. Of these, a fluorine atom, a nitro group and a cyano group are preferred.

Examples of the group (i) include groups represented by the following formulae (i-1) to (i-4), examples of the group (ii) include the group represented by the following formula (ii-1), and examples of the group (iii) include groups represented by the following formulae (iii-1) to (iii-4); and the like.

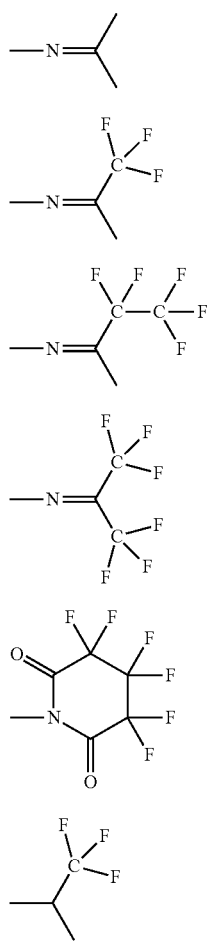

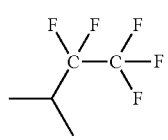

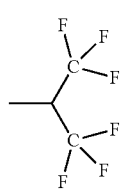

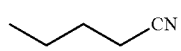

Of these, the group represented by the above formula (iii-3) and the group represented by the above formula (iii-4) are preferred.

In the above formula (d), n is an integer of preferably 2 to 5, more preferably 2 or 3, and still more preferably 2.

Examples of the polynuclear phenol include: dinuclear phenols such as 4,4'-biphenyldiol, 4,4'-methylenebisphenol, 4,4'-ethylidenebisphenol and bisphenol A; trinuclear phenols such as 4,4',4''-methylidenetrisphenol, 4,4'-(1-(4-(1-(4-hydroxyphenyl)-1-methylethyl)phenyl)ethylidene)bisphenol, and 4,4'-(1-(4-(1-(4-hydroxy-3,5-bis(methoxymethyl)phenyl)-1-methylethyl)phenyl)ethylidene)bis(2,6-bis(methoxymethyl)phenol); polyphenols such as novolak; and the like.

Examples of the alkoxymethylated melamine include hexakis(methoxymethyl)melamine, hexakis(n-butoxymethyl)melamine, and the like.

Examples of the alkoxymethylated glycoluril include 1,3,4,6-tetrakis(methoxymethyl)glycoluril, 1,3,4,6-tetrakis(n-butoxymethyl)glycoluril, and the like.

Examples of the diisocyanate include 2,3-tolylene diisocyanate, 2,4-tolylene diisocyanate, 3,4-tolylene diisocyanate, 3,5-tolylene diisocyanate, 4,4'-diphenylmethane diisocyanate, hexamethylene diisocyanate, 1,4-cyclohexane diisocyanate, and the like.

Examples of the compound (d) include compounds represented by the following formulae (d-1) to (d-4), and the like.

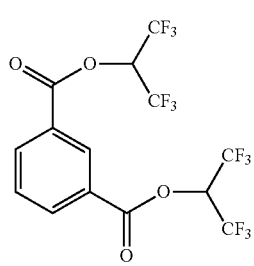

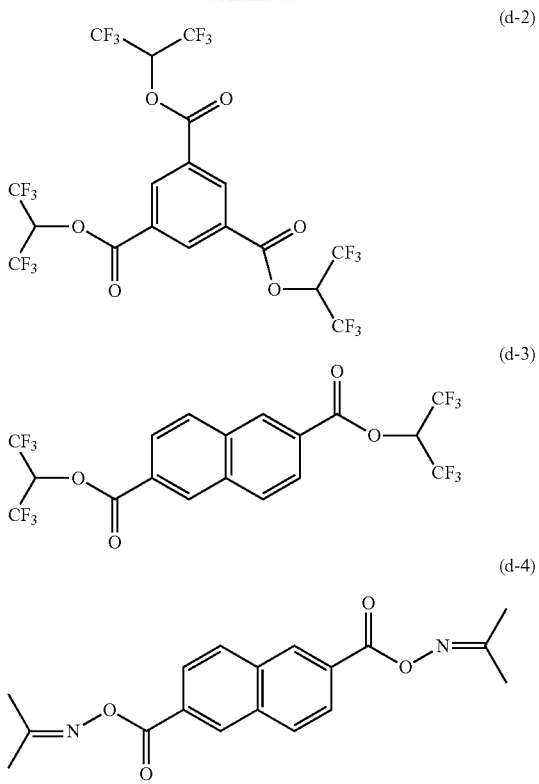

Of these, as the crosslinking agent (D), the polynuclear phenol, the alkoxymethylated glycoluril and the compound (d) which are available are preferred, and 4,4'-(1-(4-(1-(4-hydroxyphenyl)-1-methylethyl)phenyl)ethylidene)bisphenol, 1,3,4,6-tetrakis(methoxymethyl)glycoluril, and the compound represented by the above formula (d-1) (1,3-di(1,1,1,3,3,3-hexafluoropropan-2-yloxycarbonyl)benzene) are more preferred. When the aforementioned compounds are used as the crosslinking agent (D), the composition for film formation enables the heat resistance and the strength of the resulting resist underlayer film to be further improved.

Examples of the commercially available product of the crosslinking agent (D) include:

epoxy-based crosslinking agents such as "Epicoat 812", Epicoat 815, Epicoat 826, Epicoat 828, Epicoat 834, Epicoat 836, Epicoat 871, Epicoat 1001, Epicoat 1004, Epicoat 1007, Epicoat 1009, and Epicoat 1031 (all manufactured by Yuka Shell Epoxy Co., Ltd.), "Araldite 6600", Araldite 6700, Araldite 6800, Araldite 502, Araldite 6071, Araldite 6084, Araldite 6097, and Araldite 6099 (all manufactured by Ciba-Geigy), "DER 331", DER 332, DER 333, DER 661, DER 644, and DER 667 (all manufactured by Dow Chemical Company);

melamine-based crosslinking agents such as "Cymel 300", Cymel 301, Cymel 303, Cymel 350, Cymel 370, Cymel 771, Cymel 325, Cymel 327, Cymel 703, Cymel 712, Cymel 701, Cymel 272, and Cymel 202, and "Mycoat 506" and Mycoat 508 (all manufactured by Mitsui-Cyanamid Ltd.);

benzoguanamine-based crosslinking agents such as "Cymel 1123", Cymel 1123-10 and Cymel 1128, and "Mycoat 102", Mycoat 105, Mycoat 106 and Mycoat 130 (all manufactured by Mitsui-Cyanamid Ltd.);

phenol-based crosslinking agents such as "Resitop" (manufactured by Gun Ei Chemical Industry Co., Ltd.);

glycoluril-based crosslinking agents such as "Cymel 1170" and Cymel 1172 (all manufactured by Mitsui-Cyanamid Ltd.), and "Nikalac N-2702" (manufactured by Sanwa Chemical Co., Ltd.); and the like.

The content of the crosslinking agent (D) is preferably no greater than 1,000 parts by mass, more preferably 0.1 parts by mass to 500 parts by mass, still more preferably 1 part by mass to 100 parts by mass, and particularly preferably 2 parts by mass to 50 parts by mass with respect to 100 parts by mass of the compound (A). When the content of the crosslinking agent (D) falls within the above range, the heat resistance and the strength of the resist underlayer film formed from the composition for film formation can be more improved. One type, or two or more types of the crosslinking agent (D) may be used.

Other Optional Component

The composition for film formation may contain, in addition to the components (A) to (D) described above, for example, a binder resin, an accelerator, a surfactant, a radioactive ray-absorbent, a storage stabilizer, a defoaming agent, an adhesion promoter, etc., as other optional component. The composition for film formation may contain one type, or two or more types of each of the other optional components.

Binder Resin

When the composition for film formation contains the binder resin, the resist underlayer film formed can exhibit improved resistance to an organic solvent contained in a composition for forming a resist film, an intermediate layer or the like which is to be formed on the upper face of the resist underlayer film.

Although the binder resin is not particularly limited as long as it is a polymer compound, the binder resin is preferably at least one selected from the group consisting of a novolak resin, a resol resin, a styrene resin, an acenaphthylene resin, and a polyarylene resin. When any of the resins is used as the binder resin, the refractive index and the extinction coefficient of the resist underlayer film can be controlled so as to give a more appropriate value. As a result, the rectangularity of the cross-sectional shape of the resist pattern formed may be improved.

The novolak resin is exemplified by a resin obtained by allowing one, or two or more of phenolic compound(s) selected from the group consisting of: phenols such as phenol, cresol, xylenol, resorcinol, bisphenol A, p-tert-butylphenol and p-octylphenol; and naphthols such as α-naphthol, β-naphthol, 1,5-dihydroxynaphthalene and 2,7-dihydroxynaphthalene to react with an aldehyde or a divinyl compound using an acidic catalyst or the like.

The aldehyde is exemplified by: aldehydes such as formaldehyde; aldehyde sources such as paraformaldehyde and trioxane; and the like.

The divinyl compound is exemplified by divinylbenzene, dicyclopentadiene, tetrahydroindene, 4-vinylcyclohexene, 5-vinylnorborn-2-ene, α-pinene, β-pinene, limonene, 5-vinylnorbornadiene, and the like.

The resol resin is exemplified by a resin obtained by reacting the phenolic compound with the aldehyde using an alkaline catalyst, and the like.

The styrene resin is exemplified by: polystyrene; styrene copolymers such as styrene-α-methylstyrene copolymers and styrene-butadiene copolymers; and the like.

The acenaphthylene resin is exemplified by: a resin obtained by polymerizing a compound having an acenaphthylene skeleton through radical polymerization, anionic polymerization, cationic polymerization or the like in an appropriate polymerization system such as bulk polymerization or solution polymerization; and the like. In addition, the acenaphthylene resin can be obtained by, for example, reacting a polymer of a compound having an acenaphthylene skeleton with paraformaldehyde under an acidic condition, as described in paragraphs [0008] to [0031] of Japanese Unexamined Patent Application, Publication No. 2002-296789.

The polyarylene resin is exemplified by polyarylene ether, polyarylene sulfide, polyarylene ether sulfone, polyarylene ether ketone, and the like.

The binder resin preferably includes a naphthalene ring. When the binder resin has a naphthalene skeleton, the refractive index and the extinction coefficient of the resist underlayer film can be controlled so as to give a more appropriate value, and as a result, the rectangularity of the cross-sectional shape of the formed resist pattern may be further improved. In addition, the binder resin preferably includes a group having a carbon-carbon triple bond. According to the composition for film formation, when the binder resin includes the above-described group, the etching resistance and the flexural resistance of the resist underlayer film formed may be improved. Examples of the group including a carbon-carbon triple bond include an ethynyl group, a propargyl group, and the like.

The binder resin may include a crosslinkable group. When the binder resin includes the crosslinkable group, the strength of the resist underlayer film formed can be improved owing to the crosslinking between the molecules of the binder resin or between the molecule of the binder resin and the molecule of the compound (A). On the other hand, when the binder resin does not substantially include the crosslinkable group, film shrinkage that would occur in the formation of the resist underlayer film can be inhibited, and as a result, the flatness of the resist underlayer film formed can be more improved.

The weight average molecular weight (Mw) of the binder resin is preferably no less than 2,000 and no greater than 8,000, and more preferably no less than 3,000 and no greater than 7,000. When the Mw of the binder resin falls within the above range, the solvent resistance of the resist underlayer film formed from the composition for film formation can be more improved.

The ratio (Mw/Mn) of the weight average molecular weight to the number average molecular weight (Mn) of the binder resin is preferably 1 to 5, more preferably 1 to 3, and still more preferably 1 to 2.5.

The content of the binder resin is preferably no less than 5 parts by mass and no greater than 1,000 parts by mass, more preferably no less than 10 parts by mass and no greater than 700 parts by mass, and still more preferably no less than 30 parts by mass and no greater than 400 parts by mass with respect to 100 parts by mass of the compound (A). When the content of the binder resin falls within the above range, the solvent resistance of the resist underlayer film formed from the composition for film formation can be more improved.

Accelerator

The accelerator is a one-electron oxidizing agent or the like for sufficiently causing a dehydrogenation reaction required for oxidative crosslinking. The one-electron oxidizing agent as referred to means an oxidizing agent that by itself accepts one electron. For example, in the case of ammonium cerium(IV) nitrate, the cerium(IV) ion accepts one electron to be converted to a cerium(III) ion. Alternatively, a radical oxidizing agent such as halogen accepts one electron to be converted to an anion. Accordingly, an event of oxidizing a substance which should be oxidized (e.g., substrate, catalyst, etc.) by removing one electron from the substance which should be oxidized is referred to as "one-electron oxidation", and a component that accepts the one electron in this event is referred to as "one-electron oxidizing agent".

The one-electron oxidizing agent is exemplified by (a) a metal compound, (b) a peroxide, (c) a diazo compound, (d) a halogen or halogen-based acid, and the like.

Examples of the metal compound (a) include metal compounds that include cerium, lead, silver, manganese, osmium, ruthenium, vanadium, thallium, copper, iron, bismuth or nickel, and the like. Specific examples include: (a1) cerium salts (for example, quadrivalent cerium salts) such as ammonium cerium(IV) nitrate (CAN; ammonium hexanitratocerate(IV)), cerium(IV) acetate, cerium(IV) nitrate and cerium(IV) sulfate; (a2) lead compounds (for example, quadrivalent lead compounds) such as lead tetraacetate and lead(IV) oxide; (a3) silver compounds such as silver(I) oxide, silver(II) oxide, silver carbonate (Fetizon reagent) and silver nitrate; (a4) manganese compounds such as permanganate salts, activated manganese dioxide and manganese(III) salts; (a5) osmium compounds such as osmium tetroxide; (a6) ruthenium compounds such as ruthenium tetroxide; (a7) vanadium compounds such as $VOCl_3$, $VOF_3$, $V_2O_5$, $NH_4VO_3$ and $NaVO_3$; (a8) thallium compounds such as thallium(III) acetate, thallium(III) trifluoroacetate and thallium(III) nitrate; (a9) copper compounds such as copper (II) acetate, copper(II) trifluoromethanesulfonate, copper(II) trifluoroborate, copper(II) chloride and copper(I) acetate; (a10) iron compounds such as iron(III) chloride and potassium hexacyanoferrate(III); (a11) bismuth compounds such as sodium bismuthate; (a12) nickel compounds such as nickel peroxide; and the like.

Examples of the peroxide (b) include: peracids such as peracetic acid and m-chloroperbenzoic acid; hydroxyperoxides, e.g., hydrogen peroxide, and alkyl hydroxyperoxides such as t-butyl hydroperoxide; diacyl peroxides, peracid esters, peracid ketals, peroxydicarbonate salts, dialkyl peroxides, peracid ketones, and the like.

Examples of the diazo compound (c) include 2,2'-azobisisobutyronitrile, and the like.

Examples of the halogen or halogen-based acid (d) include: halogens selected from chlorine, bromine and iodine; perhalic acids, halic acids, halous acids, hypohalogenous acid, and salts thereof; and the like. It is to be noted that the halogen in the halogen-based acid is exemplified by chlorine, bromine and iodine. Moreover, specific examples of the halogen-based acid or the salt thereof include sodium perchlorate, sodium bromate, and the like.

Of these one-electron oxidizing agents, the peroxide (b) and the diazo compound (c) are preferred, and m-chloroperbenzoic acid, t-butyl hydroperoxide and 2,2'-azobisisobutyronitrile are more preferred. When these are used, metal residues and the like are less likely to adhere to the substrate.

The content of the accelerator is preferably no greater than 1,000 parts by mass, more preferably 0.01 parts by mass to 500 parts by mass, and still more preferably 0.1 parts by mass to 100 parts by mass with respect to 100 parts by mass of the compound (A).

Surfactant

The surfactant is a component that exhibits the effects of improving application properties, striation, wettability, developability and the like of the composition for film formation. The content of the surfactant is preferably no greater than 15 parts by mass, and more preferably no greater than 10 parts by mass with respect to 100 parts by mass of the compound (A). One type, or two or more types of the surfactant may be used.

Preparation Method of Composition for Film Formation

The composition for film formation may be prepared, for example, by mixing the compound (A) and the solvent (B), as well as the optional component(s) which may be contained as needed, at a certain ratio. The composition for film formation is preferably filtered through a filter of about 0.1 µm, for example, after the mixing. The solid content concentration of the composition for film formation is preferably 0.1% by mass to 50% by mass, more preferably 0.5% by mass to 30% by mass, and still more preferably 1% by mass to 20% by mass. The concentration of the compound (A) in the composition for film formation is preferably 0.1% by mass to 30% by mass, more preferably 0.5% by mass to 20% by mass, and still more preferably 1% by mass to 15% by mass.

The viscosity of the composition for film formation at a solid content concentration of 20% by mass is preferably no less than 1 cps and no greater than 5 cps, and more preferably no less than 1 cps and no greater than 3 cps. When the value of the viscosity of the composition for film formation falls within the above range, filling performances of the composition for film formation may be improved, and the flatness of the resist underlayer film formed may be improved.

Resist Underlayer Film-Forming Method

The resist underlayer film-forming method according to another embodiment of the present invention includes the steps of:

providing a coating film on the upper face side of a substrate (hereinafter, may be also referred to as "coating film-providing step"); and baking the coating film (hereinafter, may be also referred to as "baking step"). The coating film is provided by using the composition for film formation according to the embodiment of the present invention.

According to the resist underlayer film-forming method, since the composition for film formation described above is used, formation of a resist underlayer film exhibiting superior heat resistance and superior flatness is enabled. In addition, the resist underlayer film-forming method can also be suitably applied to stepped substrates and substrates having a plurality of kinds of trenches, and form a resist underlayer film superior in flatness.

Each step will be explained below.

Coating Film-Providing Step

In this step, a coating film is provided on the upper face side of a substrate by using the composition for film formation.

The substrate is exemplified by a silicon wafer, a wafer coated with aluminum, and the like.

As described above, in the pattern-forming method, the stepped substrates, the substrates having a plurality of kinds of trenches, and the like can also be suitably used, and a resist underlayer film superior in flatness can be formed.

For example, substrates having trenches with aspect ratios that differ from one another can also be suitably used as the substrates having a plurality of kinds of trenches. Substrates that involve various values of the aspect ratio may also be used; for example, the ratio of the maximum value to the minimum value of the aspect ratios of the trenches of the substrate is preferably no less than 3, more preferably no less than 5, still more preferably no less than 10, and particularly preferably no less than 15.

The procedure for applying the composition for film formation onto the substrate is not particularly limited, and applying the composition for film formation may be carried out by an appropriate procedure such as, for example, spin-coating, cast-coating, or roll-coating.

The thickness of the coating film thus provided is preferably 100 nm to 5 µm, and more preferably 200 nm to 3 µm.

Baking Step

In this step, the coating film provided in the coating film-providing step is baked. The procedure for baking the coating film is exemplified by a method involving heating, and the like. The temperature of this heating is preferably 100° C. to 400° C., more preferably 200° C. to 390° C., and still more preferably 300° C. to 370° C. The heating time period is preferably 5 sec to 60 min, more preferably 10 sec to 10 min, and still more preferably 30 sec to 3 min. This heating may be carried out in an atmosphere, for example, in air, or in an inert gas such as a nitrogen gas or an argon gas.

The thickness of the resist underlayer film thus formed is preferably 10 nm to 5 µm, and more preferably 30 nm to 500 µm.

Pattern-Forming Method

The pattern-forming method according to still another embodiment of the present invention includes the steps of:

forming a resist pattern on the upper face side of a resist underlayer film (hereinafter, may be also referred to as "resist pattern-forming step"); and sequentially etching the resist underlayer film and a substrate using the resist pattern as a mask (hereinafter, may be also referred to as "etching step").

The resist underlayer film is formed by the resist underlayer film-forming method of the another embodiment of the present invention.

Moreover, according to the pattern-forming method, the resist pattern-forming step preferably includes forming an intermediate layer on the upper face side of the resist underlayer film, and forming the resist pattern on the upper face side of the intermediate layer, and the etching step preferably further includes etching the intermediate layer.

According to the pattern-forming method, since the resist underlayer film formed from the composition for film formation described above and exhibiting superior heat resistance and superior flatness is used, a favorable pattern can be formed.

Each step will be explained below.

Resist Pattern-Forming Step

In this step, a resist pattern is formed on the upper face side of the resist underlayer film described above. An intermediate layer may be formed on the upper face side of the resist underlayer film, and the resist pattern may be formed on the upper face side of the intermediate layer.

The intermediate layer has functions exhibited by the resist underlayer film and/or the resist film in the resist pattern formation, etc. for the purpose of reinforcing the abovementioned functions, or has functions not exhibited by the resist underlayer film and/or the resist film in the resist pattern formation, etc. for the purpose of imparting the unexhibited functions. For example, in a case where an antireflective film is provided as the intermediate layer, a reflection-preventive function of the resist underlayer film can be reinforced.

The intermediate layer may be provided by using an organic compound or an inorganic oxide. Examples of the organic compound include materials commercially available from Brewer Science, Inc. under the tradename "DUV-42", "DUV-44", "ARC-28", "ARC-29" and the like, and materials commercially available from Rohm & Haas Company under the trade name "AR-3", "AR-19" and the like, etc.

Moreover, as the inorganic oxide, materials commercially available from JSR Corporation under the trade name "NFC SOG" series and the like, and polysiloxanes, titanium oxide, oxidized alumina, tungsten oxide, and the like which are formed by a CVD process may be used.

The procedure for providing the intermediate layer is exemplified by, but not particularly limited to, a coating procedure, a CVD process, and the like. Of these, the coating procedure is preferred. In a case where the coating procedure is employed, the intermediate layer can be provided consecutively after forming the resist underlayer film.

Moreover, although the film thickness of the intermediate layer is not particularly limited and appropriately selected in accordance with the functions required for the intermediate layer, the film thickness of the intermediate layer is preferably 10 nm to 3 µm, and more preferably 20 nm to 0.3 µm.

The procedure for forming the resist pattern on the upper face side of the resist underlayer film or the intermediate layer is exemplified by a procedure involving photolithography, and the like. This procedure will be explained in more detail below.

An exemplary procedure involving photolithography includes the steps of:

forming a resist film from a resist composition on the upper face side of a resist underlayer film (hereinafter, may be also referred to as "resist film-forming step");

exposing the resist film (hereinafter, may be also referred to as "exposure step"); and developing the resist film exposed (hereinafter, may be also referred to as "development step").

Resist Film-Forming Step

In this step, a resist film is formed from a resist composition on the upper face side of a resist underlayer film. Specifically, after the resist composition is applied such that the resulting resist film has a predetermined thickness, prebaking is executed to evaporate the solvent in the coating film, whereby the resist film is formed.

The resist composition is exemplified by: a positive type or negative type chemically amplified resist composition which contains a photoacid generating agent; a positive type resist composition which contains an alkali-soluble resin and a quinone diazide-type photosensitizing agent; a negative type 1 to resist composition which contains an alkali-soluble resin and a crosslinking agent; and the like.

The solid content concentration of the resist composition is preferably 5 to 50% by mass. In addition, the resist composition is preferably prepared after filtration thereof through a filter having a pore size of about 0.2 µm. It is to be noted that in this step, a commercially available resist composition may be directly used.

The procedure for applying the resist composition is not particularly limited, and applying the resist composition may be carried out by an appropriate procedure such as, for example, spin-coating, cast-coating, or roll-coating.

Moreover, the prebaking temperature may be appropriately selected in accordance with the type of the resist composition used and the like, but is preferably 30° C. to 200° C., and more preferably 50° C. to 150° C.

Exposure Step

In this step, the resist film formed in the resist film-forming step is exposed. For example, this exposure is executed through a certain mask pattern, and a liquid immersion liquid, as needed.

The exposure light may be appropriately selected in accordance with the type of the photoacid generating agent used in the resist composition, from e.g., electromagnetic waves such as visible light rays, ultraviolet rays, far ultraviolet rays, X-rays and γ-rays; particle rays such as electron beams, molecular beams, ion beams and α-rays; and the like. However, far ultraviolet rays are preferred; a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) and an extreme-ultraviolet ray (wavelength: 13 nm, etc.) are more preferred, and an ArF excimer laser beam is still more preferred.

In order to improve the resolution, the pattern profile, the developability, etc. of the formed resist pattern, post-baking may be executed after the exposure. The temperature of this post-baking may be appropriately adjusted in accordance with the type of the type of the resist composition used and the like, but is preferably 50° C. to 200° C., and more preferably 70° C. to 150° C.

Development Step

In this step, the resist film exposed in the exposure step is developed.

The developer solution which may be used in the development may be appropriately selected in accordance with the type of the resist composition used. For a development with an alkali, specific examples of the developer solution include alkaline aqueous solutions of: sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, and 1,5-diazabicyclo[4.3.0]-5-nonene, and the like. It is to be noted that in a case where the step of forming the intermediate layer is executed to form the intermediate layer, the influence of these alkaline aqueous solutions on the resist underlayer film can be minimized.

An appropriate amount of a water soluble organic solvent, for example, an alcohol such as methanol or ethanol, and/or a surfactant may be added to these alkaline aqueous solutions.

Moreover, a developer solution which contains an organic solvent may be used as the developer solution. Examples of the organic solvent include esters, ketones, ethers, alcohols, amides, hydrocarbons, and the like. The development with an organic solvent has a minor influence on the resist underlayer film.

Subsequent to the development with the developer solution, washing and drying are executed, whereby a predetermined resist pattern is formed.

Moreover, a procedure involving nanoimprinting, a procedure involving the use of a directed self-assembling composition, and the like may also be used as the procedure for executing the resist pattern-forming step in place of the procedure involving photolithography described above.

Etching Step

In this step, the resist underlayer film and the substrate are sequentially etched using the resist pattern as a mask such that the substrate has a pattern. It is to be noted that in a case where the intermediate layer is formed, the intermediate layer is also dry-etched.

The etching may be executed through either dry-etching or wet-etching.

The dry-etching may be executed using a well-known dry-etching apparatus. In addition, depending on the elemental composition of a substance to be etched, the following gases may be used as a source gas in the dry-etching: oxygen atom-containing gases such as $O_2$, CO and $CO_2$; inert gases such as He, $N_2$ and Ar; chlorine-based gases such as $Cl_2$ and $BCl_3$; fluorine-based gases such as $CHF_3$ and $CF_4$; other gases such as $H_2$ as $NH_3$; and the like. It is to be noted that these gases may also be used as a mixture.

EXAMPLES

Hereinafter, the embodiments of the present invention will be explained in more detail by way of Examples, but the present invention is not in any way limited to these Examples.

It is to be noted that the polystyrene equivalent weight average molecular weight (Mw) of the compound was determined by gel permeation chromatography using GPC columns ("G2000 HXL"×2, and "G3000 HXL"×1 available from Tosoh Corporation), a differential refractometer as a detector, and mono-dispersed polystyrene as a standard under analytical conditions involving a flow rate of 1.0 mL/min, an elution solvent of tetrahydrofuran, and a column temperature of 40° C. In addition, the thickness of each film was measured using a spectroscopic ellipsometer ("M2000D" available from J. A. WOOLLAM).

Synthesis of Compound (A)

Synthesis Example 1

Synthesis of Compound (A-1)

In a separable flask equipped with a thermometer, 100 parts by mass of 1,3,5-tris(p-bromophenyl)benzene, 60 parts by mass of ethynylbenzene, 7 parts by mass of dichlorobis(triphenylphosphine)palladium(II), 2 parts by mass of copper(I) iodide, 100 parts by mass of triethylamine, and 600 parts by mass of tetrahydrofuran as a solvent were mixed in a nitrogen atmosphere, and a reaction was allowed to proceed at 70° C. for 4 hrs with stirring to give a reaction liquid. After the reaction liquid thus obtained was filtered, methanol was added thereto to permit reprecipitation. The precipitates thus obtained were dissolved in ethyl acetate, and the solution was sequentially washed with dilute hydrochloric acid and an aqueous sodium bicarbonate solution, followed by drying the organic layer, whereby a compound represented by the following formula (A-1) was obtained.

Synthesis Example 2

Synthesis of Compound (A-2)

A compound represented by the following formula (A-2) was obtained in a similar manner to Synthesis Example 1 except that 35 parts by mass of 2-propyn-1-ol were used in place of 60 parts by mass of ethynylbenzene used in Synthesis Example 1.

Synthesis Example 3

Synthesis of Compound (A-3)

A compound represented by the following formula (A-3) was obtained in a similar manner to Synthesis Example 1 except that 50 parts by mass of 1-hexyne were used in place of 60 parts by mass of ethynylbenzene used in Synthesis Example 1.

Synthesis Example 4

Synthesis of Compound (A-4)

A compound represented by the following formula (A-4) was obtained in a similar manner to Synthesis Example 1 except that 50 parts by mass of 2-methyl-3-butyn-2-ol were used in place of 60 parts by mass of ethynylbenzene used in Synthesis Example 1.

Synthesis Example 5

Synthesis of Compound (A-5)

A compound represented by the following formula (A-5) was obtained in a similar manner to Synthesis Example 1 except that 130 parts by mass of 1,1-diphenyl-2-propyn-1-ol were used in place of 60 parts by mass of ethynylbenzene used in Synthesis Example 1.

Synthesis Example 6

Synthesis of Compound (A-6)

A compound represented by the following formula (A-6) was obtained in a similar manner to Synthesis Example 1 except that 70 parts by mass of 3-ethynylaniline were used in place of 60 parts by mass of ethynylbenzene used in Synthesis Example 1.

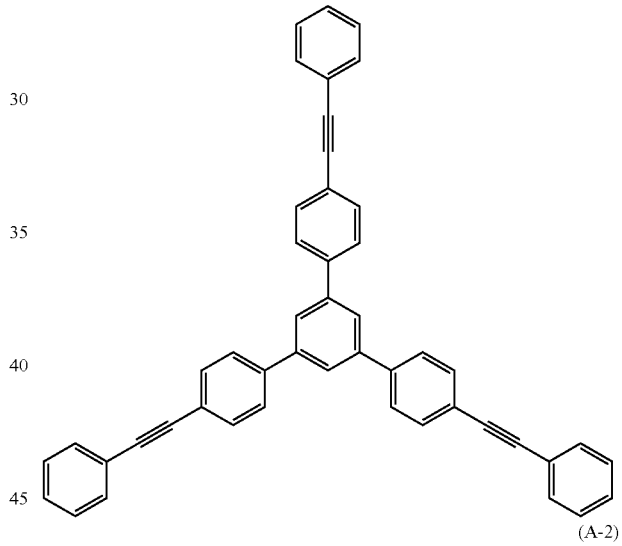

(A-1)

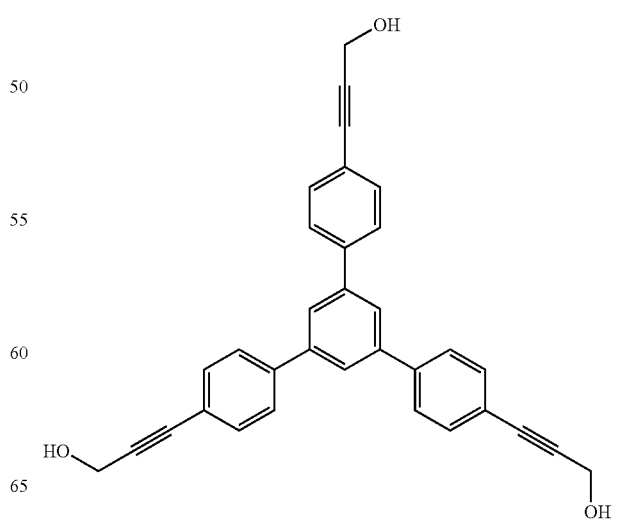

(A-2)

(A-3)

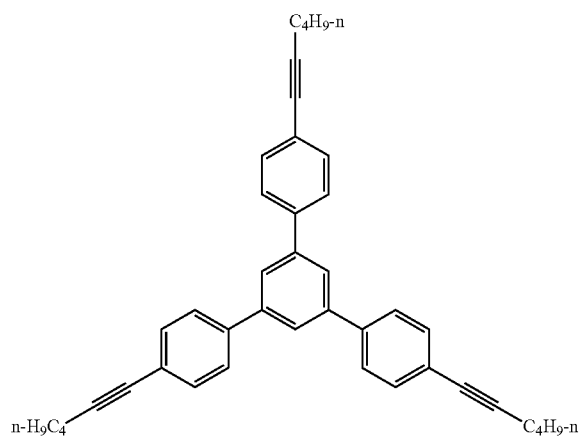

(A-4)

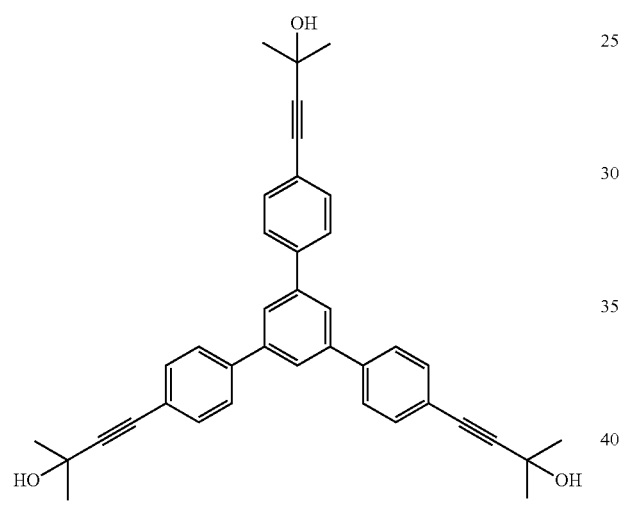

(A-5)

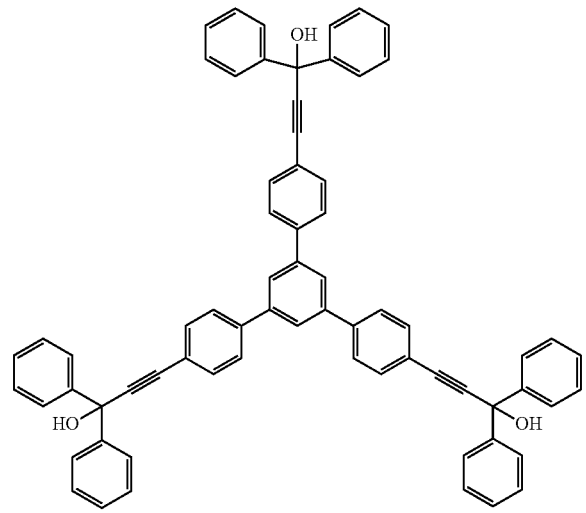

(A-6)

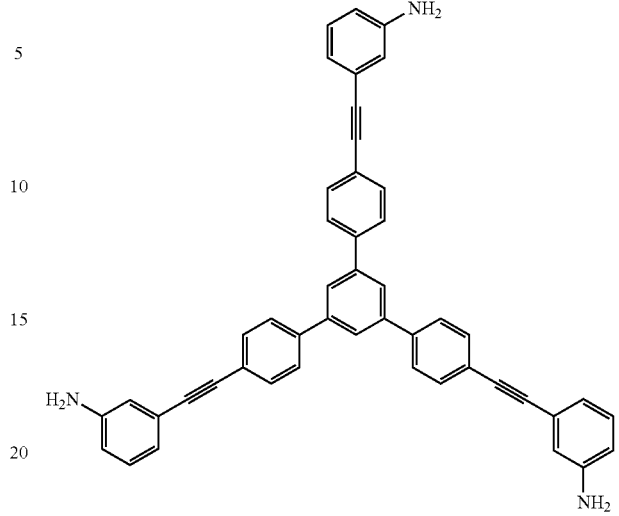

Synthesis Example 7

Synthesis of Compound (A-7)

In a separable flask equipped with a thermometer, 100 parts by mass of 1,3,5-tris(4'-bromobiphenyl-4-yl)benzene, 42 parts by mass of trimethylsilylacetylene, 5 parts by mass of dichlorobis(triphenylphosphine)palladium(II), 2 parts by mass of copper(I) iodide, 100 parts by mass of triethylamine and 600 parts by mass of tetrahydrofuran as a solvent were mixed in a nitrogen atmosphere, and a reaction was allowed to proceed at 70° C. for 4 hrs with stirring to give a reaction liquid. After the reaction liquid was filtered, methanol was added thereto to permit reprecipitation. The precipitates thus obtained were dissolved in ethyl acetate, and the solution was sequentially washed with dilute hydrochloric acid and an aqueous sodium bicarbonate solution, followed by concentrating the organic layer, whereby a dried matter was obtained. Next, 80 parts by mass of potassium carbonate, 400 parts by mass of tetrahydrofuran and 150 parts by mass of methanol were added to the dried matter thus obtained, and a reaction was allowed to proceed at room temperature for 4 hrs. After the reaction liquid thus obtained was filtered, ethyl acetate was added thereto, and the solution was sequentially washed with dilute hydrochloric acid and an aqueous sodium bicarbonate solution, followed by concentrating the organic layer, whereby a compound (A-7) represented by the following formula was obtained.

(A-7)

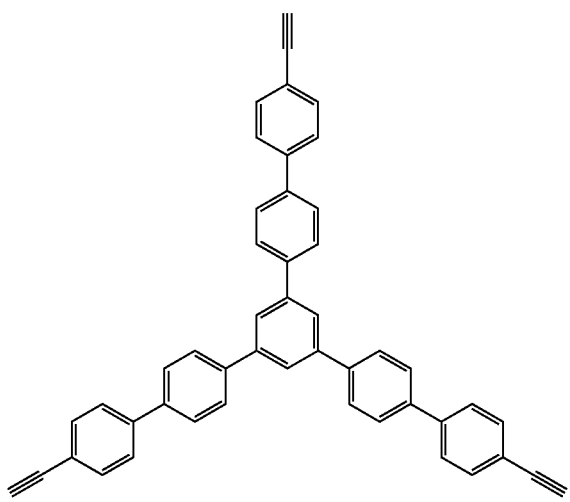

Comparative Synthesis Example 1

Synthesis of Compound (a-1)

Into a separable flask equipped with a thermometer were charged 100 parts by mass of 2,7-dihydroxynaphthalene, 30 parts by mass of formalin, 1 part by mass of p-toluenesulfonic acid, and 150 parts by mass of propylene glycol monomethyl ether in a nitrogen atmosphere, and polymerization was allowed at 80° C. for 6 hrs with stirring to give a reaction liquid. The reaction liquid thus obtained was diluted with 100 parts by mass of n-butyl acetate, and the organic layer was washed with a large amount of a mixed solvent of water and methanol (mass ratio: water/methanol=1/2). The solvent was distilled off from the organic layer thus obtained, whereby a compound (a-1) which was a polymer having a structural unit represented by the following formula (a-1) was obtained. The compound (a-1) had an Mw of 1,800.

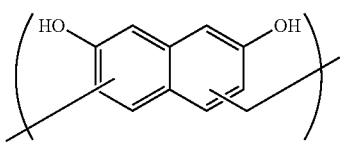

(a-1)

Preparation of Composition for Film Formation

Components other than the compound (A) which constituted the composition for film formation are shown below.

(B) Solvent

B-1: cyclohexanone (C) Acid Generating Agent

C-1: bis(t-butylphenyl)iodonium nonafluoro-n-butanesulfonate (a compound represented by the following formula (C-1))

(C-1)

(D) Crosslinking Agent

D-1: "Nikalac N-2702" available from Sanwa Chemical Co., Ltd. (a compound represented by the following formula (D-1))

D-2: 4,4'-(1-(4-(1-(4-hydroxy-3,5-bis(methoxymethyl)phenyl)-1-methylethyl)phenyl)ethylidene)bis(2,6-bis(methoxymethyl)phenol (a compound represented by the following formula (D-2))

D-3: 1,3-di(1,1,1,3,3,3-hexafluoropropan-2-yloxycarbonyl)benzene (a compound represented by the following formula (D-3))

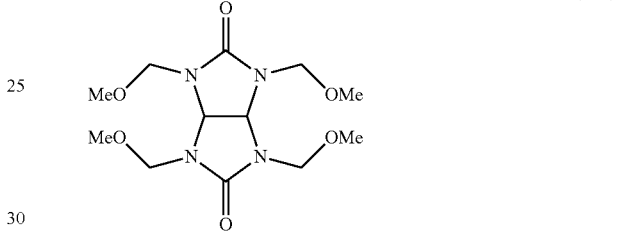

(D-1)

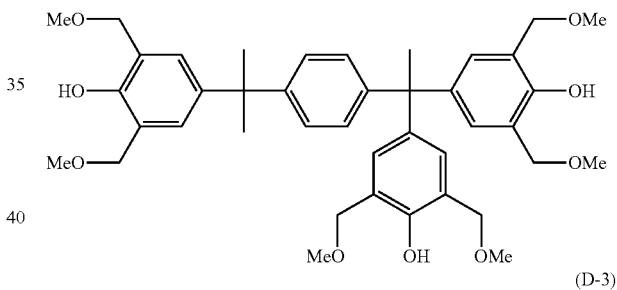

(D-2)

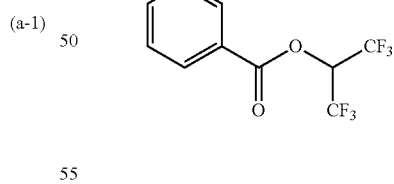

(D-3)

Example 1

A solution was prepared by mixing 10 parts by mass of (A-1) as the compound (A) and 100 parts by mass of (B-1) as the solvent (B). This solution was filtered through a membrane filter having a pore size of 0.1 μm, and thereby a composition for film formation (J-1) was prepared.

Examples 2 to 9 and Comparative Example 1

Compositions for film formation (J-2) to (J-9) and (CJ-1) were prepared in a similar manner to Example 1 except that the type and the content of each component were as shown in Table 1. It is to be noted that "-" in Table 1 indicates that the corresponding component was not used.

TABLE 1

| Composition for film formation | (A) Compound | | (B) Solvent | | (C) Acid generating agent | | (D) Crosslinking agent | |
|---|---|---|---|---|---|---|---|---|
| | type | content (parts by mass) | type | content (parts by mass) | type | content (parts by mass) | type | content (parts by mass) |
| Example 1 | J-1 | A-1 | 10 | B-1 | 100 | — | — | — | — |
| Example 2 | J-2 | A-2 | 10 | B-1 | 100 | — | — | — | — |
| Example 3 | J-3 | A-3 | 10 | B-1 | 100 | — | — | — | — |
| Example 4 | J-4 | A-4 | 10 | B-1 | 100 | — | — | — | — |
| Example 5 | J-5 | A-5 | 10 | B-1 | 100 | — | — | — | — |
| Example 6 | J-6 | A-6 | 10 | B-1 | 100 | — | — | — | — |
| Example 7 | J-7 | A-1 | 10 | B-1 | 100 | C-1 | 0.5 | D-1 | 1 |
| Example 8 | J-8 | A-1 | 10 | B-1 | 100 | C-1 | 0.5 | D-2 | 1 |
| Example 9 | J-9 | A-1 | 10 | B-1 | 100 | C-1 | 0.5 | D-3 | 1 |
| Comparative Example 1 | CJ-1 | a-1 | 10 | B-1 | 100 | — | — | — | — |

Examples 10 to 13

Compositions for film formation (J-10) to (J-13) were prepared in a similar manner to Example 1 except that the type and the content of each component were as shown in Table 2. It is to be noted that "-" in Table 2 indicates that the corresponding component was not used.

TABLE 2

| Composition for film formation | (A) Compound | | (B) Solvent | | (C) Acid generating agent | | (D) Croslinking agent | |
|---|---|---|---|---|---|---|---|---|
| | type | content (parts by mass) | type | content (parts by mass) | type | content (parts by mass) | type | content (parts by mass) |
| Example 10 | J-10 | A-7 | 10 | B-1 | 100 | — | — | — | — |
| Example 11 | J-11 | A-7 | 10 | B-1 | 100 | C-1 | 0.5 | D-1 | 1 |
| Example 12 | J-12 | A-7 | 10 | B-1 | 100 | C-1 | 0.5 | D-2 | 1 |
| Example 13 | J-13 | A-7 | 10 | B-1 | 100 | C-1 | 0.5 | D-3 | 1 |

Evaluations

The compositions for film formation obtained above or the substrates having a resist underlayer film obtained therefrom were evaluated for the following items in accordance with the following methods. The results of the evaluations are shown in Tables 3 and 4.

Refractive Index and Extinction Coefficient

Each composition for film formation prepared above was spin-coated on the surface of a silicon wafer having a diameter of 8 inches, i.e., a substrate, to provide a coating film, and the coating film was baked in air at 350° C. for 2 min, whereby a resist underlayer film having a thickness of 250 nm was formed. The refractive index and the extinction coefficient of the formed resist underlayer film at a wavelength of 193 nm were measured using a spectroscopic ellipsometer ("M2000D" available from J. A. WOOLLAM). In these evaluations, the optical characteristics can be evaluated as being "favorable" in a case where the refractive index was no less than 1.3 and no greater than 1.6 and the extinction coefficient was no less than 0.2 and no greater than 0.8.

Etching Resistance

First, the composition for film formation was spin-coated on a silicon wafer having a diameter of 8 inches by a spin-coating procedure to form an underlayer film having a thickness of 300 nm. Thereafter, the underlayer film was subjected to an etching treatment (pressure: 0.03 Torr; high frequency power: 3,000 W; $Ar/CF_4=40/100$ sccm; and substrate temperature: 20° C.), and the thickness of the underlayer film after the etching treatment was measured. Then, the etching rate (nm/min) was calculated from a relationship between a decrease of the thickness of the film and the treatment time period, and the proportion of the etching rate of the film according to Examples with respect to that of the film according to Comparative Example was calculated. The smaller value indicates more favorable etching resistance.

Heat Resistance

Each composition for film formation was spin-coated on a silicon wafer having a diameter of 8 inches to provide a coating film (resist underlayer film), and the thickness of the coating film was measured using the spectroscopic ellipsometer (the value of the thickness acquired in this measurement being designated as X). Next, the resist underlayer film was heated at 350° C. for 120 sec, and the thickness of the resist underlayer film after the heating was measured using the spectroscopic ellipsometer (the value of the thickness acquired in this measurement being designated as Y). Then, a percent 1 to decrease $\Delta FT$ (%) of the thickness of the resist underlayer film after the heating with respect to the thickness of the resist underlayer film before the heating ($\Delta FT (\%) = 100 \times (X-Y)/X$) was calculated, and the calculated value was defined as heat resistance (%). It is to be noted that the smaller value of the heat resistance (%) indicates that a less amount of sublimated matter and film degradation products would have been generated during the heating of the resist underlayer film, and that the resist underlayer film exhibits more superior heat resistance and is more favorable.

Flatness

The composition for film formation of Examples and Comparative Example were each applied onto a SiO$_2$ stepped substrate provided with trenches having a width of 42 nm, a pitch of 84 nm and a depth of 180 nm (aspect ratio: 4.3), trenches having a width of 100 nm, a pitch of 150 nm and a depth of 180 nm (aspect ratio: 1.8), and trenches (open space) having a width of 5 μm and a depth of 180 nm (aspect ratio: 0.036) in combination, with the ratio of the maximum value to the minimum value of the aspect ratios that differ from one another being 119. Thereafter, baking was carried out at 250° C. for 60 sec under an ambient air atmosphere to form a resist underlayer film having a thickness of 200 nm. The shape of the resist underlayer film was observed using a scanning electron microscope (S-4800, manufactured by Hitachi High-Technologies Corporation), and the difference (ΔFT) of the maximum value and the minimum value of the thickness of the resist underlayer film on the trenches or spaces was determined. The flatness of the resist underlayer film was evaluated as being "A" (favorable) in a case where the ΔFT was less than 20 nm; and "B" (unfavorable) in a case where the ΔFT was no less than 20 nm.

The results of the evaluations are shown in Table 3 for the compositions for film formation according to Examples 1 to 9, and in Table 4 for the compositions for film formation according to Examples 10 to 13.

TABLE 3

| | Composition for film formation | Refractive index | Extinction coefficient | Etching resistance | Heat resistance (%) | Flatness |
|---|---|---|---|---|---|---|
| Example 1 | J-1 | 1.40 | 0.60 | 0.70 | 8 | A |
| Example 2 | J-2 | 1.42 | 0.50 | 0.80 | 10 | A |
| Example 3 | J-3 | 1.43 | 0.55 | 0.75 | 11 | A |
| Example 4 | J-4 | 1.42 | 0.55 | 0.80 | 10 | A |
| Example 5 | J-5 | 1.41 | 0.65 | 0.75 | 9 | A |
| Example 6 | J-6 | 1.40 | 0.58 | 0.70 | 8 | A |
| Example 7 | J-7 | 1.40 | 0.58 | 0.75 | 8 | A |
| Example 8 | J-8 | 1.42 | 0.62 | 0.75 | 8 | A |
| Example 9 | J-9 | 1.45 | 0.60 | 0.82 | 8 | A |
| Comparative Example 1 | CJ-1 | 1.40 | 0.40 | 1.00 | 20 | B |

TABLE 4

| | Composition for film formation | Refractive index | Extinction coefficient | Etching resistance | Heat resistance (%) | Flatness |
|---|---|---|---|---|---|---|
| Example 10 | J-10 | 1.42 | 0.45 | 0.75 | 6 | A |
| Example 11 | J-11 | 1.40 | 0.45 | 0.78 | 7 | A |
| Example 12 | J-12 | 1.41 | 0.48 | 0.78 | 7 | A |
| Example 13 | J-13 | 1.41 | 0.46 | 0.83 | 7 | A |
| Comparative Example 1 | CJ-1 | 1.40 | 0.40 | 1.00 | 20 | B |

As is clear from Table 3 and Table 4, the resist underlayer films formed from the compositions for film formation of Examples satisfy the requirements for general characteristics such as the refractive index, the extinction coefficient and the etching resistance, and additionally exhibit more superior heat resistance and flatness as compared with the resist underlayer film formed from the composition for film formation of Comparative Example.

The composition for film formation and the resist underlayer film-forming method according to the embodiments of the present invention enable the formation of a resist underlayer film that exhibits superior heat resistance and superior flatness while satisfying the requirements for the general characteristics such as the optical characteristics and the etching resistance. The resist underlayer film according to the embodiment of the present invention exhibits superior heat resistance and superior flatness while satisfying the requirements for the general characteristics such as the optical characteristics and the etching resistance. According to the pattern-forming method of the embodiment of the present invention, since the resist underlayer film exhibiting superior heat resistance and superior flatness is used, a favorable pattern can be formed. The compound according to the embodiment of the present invention can be particularly suitably used as a component of the composition for film formation. Therefore, these can be suitably used in pattern formation that employs a multilayer resist process in the production of semiconductor devices in which microfabrication of patterns has been further in progress. Moreover, the composition for film formation according to the embodiment of the present invention can be suitably used in the aerospace industry in which superior heat resistance is required.

Obviously, numerous modifications and variations of the present invention are possible in light of the above teachings. It is therefore to be understood that within the scope of the appended claims, the invention may be practiced otherwise than as specifically described herein.

The invention claimed is:
1. A pattern-forming method comprising:
applying a composition on an upper face side of a substrate to form a resist underlayer film;
baking the resist underlayer film;
forming a resist pattern on an upper face side of the resist underlayer film; and
sequentially etching the resist underlayer film and a substrate using the resist pattern as a mask,
wherein the composition comprises:
a compound represented by formula (1); and
a solvent,

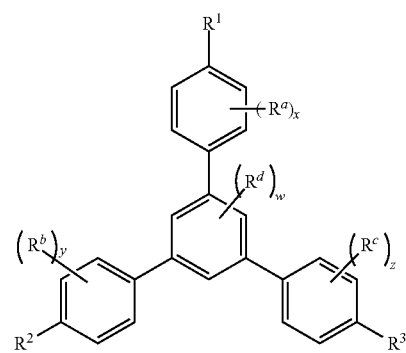

(1)

wherein in the formula (1),
R$^1$, R$^2$ and R$^3$ each independently represent a group represented by formula (a), wherein R$^1$, R$^2$ and R$^3$ are identical or different;

$R^a$, $R^b$, $R^c$ and $R^d$ each independently represent a halogen atom, a hydroxy group, an amino group, a sulfanyl group, or a monovalent organic group having 1 to 20 carbon atoms and not comprising an aromatic ring;

x, y and z are each independently an integer of 0 to 4; and w is an integer of 0 to 3, wherein in a case where $R^a$ to $R^d$ are each present in a plurality of number, a plurality of $R^a$s are identical or different, a plurality of $R^b$s are identical or different, a plurality of $R^c$s are identical or different, and a plurality of $R^d$s are identical or different,

 (a)

wherein in the formula (a), $R^A$ represents a hydrogen atom, an aryl group, or an alkyl group unsubstituted or substituted with at least one of a hydroxy group and an aryl group; and $R^B$ represents a single bond or an arylene group, wherein a part or all of hydrogen atoms on an aromatic ring of the aryl group and the arylene group are unsubstituted or substituted with a halogen atom, a hydroxy group, an amino group, a sulfanyl group, or a monovalent organic group having 1 to 20 carbon atoms and not comprising an aromatic ring.

2. The pattern-forming method according to claim 1, wherein the forming of the resist pattern comprises forming an intermediate layer on the upper face side of the resist underlayer film, and forming the resist pattern on an upper face side of the intermediate layer, and the etching further comprises etching the intermediate layer.

3. The pattern-forming method according to claim 1, wherein a molecular weight of the compound is no less than 400 and no greater than 1,000.

4. The pattern-forming method according to claim 1, wherein the composition further comprises a crosslinking agent.

5. The pattern-forming method according to claim 1, wherein a carbon percentage content of the compound is no less than 50 atom %.

6. The pattern-forming method according to claim 1, wherein in the formula (a), $R^A$ represents a hydrogen atom, an aryl group, or an alkyl group unsubstituted or substituted with an aryl group.

7. The pattern-forming method according to claim 1, wherein in the formula (a), at least one $R^A$ represents a hydrogen atom.

8. The pattern-forming method according to claim 1, wherein in the formula (a), at least two $R^A$s represent a hydrogen atom.

9. The pattern-forming method according to claim 1, wherein in the formula (a), $R^A$ represents a hydrogen atom.

10. The pattern-forming method according to claim 1, wherein a content of the compound in the composition is no less than 80% by mass with respect to a total solid content of the composition.

11. The pattern-forming method according to claim 1, wherein a content of the compound in the composition is no less than 90% by mass with respect to a total solid content of the composition.

12. The pattern-forming method according to claim 1, wherein a content of the compound in the composition is no less than 95% by mass with respect to a total solid content of the composition.

\* \* \* \* \*